United States Patent [19]

Kauffman et al.

[11] Patent Number: 5,587,112
[45] Date of Patent: Dec. 24, 1996

[54] BENZAZOLE COMPOUNDS WITH ESIPT FLUORESCENCE

[75] Inventors: Joel M. Kauffman, Wayne; Peter T. Litak, Lansdowne, both of Pa.

[73] Assignee: Philadelphia College of Pharmacy and Science, Philadelphia, Pa.

[21] Appl. No.: 300,401

[22] Filed: Sep. 2, 1994

[51] Int. Cl.$^6$ .............................. F21V 9/04; C09K 11/06; C07D 277/62
[52] U.S. Cl. .................. 252/589; 252/582; 252/587; 252/301.16; 252/301.17; 252/301.35; 548/156; 548/159; 548/217; 548/224; 548/305.1
[58] Field of Search ................... 252/582, 600, 252/301.16, 301.17, 301.31, 301.32, 301.35, 587, 589; 548/156, 159, 217, 224, 305.1

[56] References Cited

U.S. PATENT DOCUMENTS

| | | | |
|---|---|---|---|
| 2,737,516 | 3/1956 | Sartori | 260/304 |
| 3,293,258 | 12/1966 | Slegrist et al. | 260/307 |
| 3,314,894 | 4/1967 | Nyilas et al. | 252/301.2 |
| 3,575,996 | 4/1971 | Liechti et al. | 260/307 |
| 3,673,202 | 6/1972 | Orlando et al. | 260/304 |
| 3,872,094 | 3/1975 | Meyer | 548/217 |
| 4,594,179 | 6/1986 | Harrah et al. | 252/301.17 |
| 5,298,189 | 3/1994 | Kauffman | 252/301.17 |

OTHER PUBLICATIONS

Pla–Dalmau, Chemical Abstracts 122:117120, (1994), Abstract of Mater. Res. Soc. Symp. Proc., (1994), pp. 163–172.
Kaufmann, Chemical Abstracts 123:231284, (1995), Abstract of Scifi 93, Workshop Scintill. Fiber Dect., (1993), pp. 353–360.
Kasha et al., Proceedings of the Workshop on Radiation Hardness of Plastic Scintillator, Mar. 19–21, Tallahassee, Fla., pp. 49–60 (1990).
Clough et al., Proceedings of the Workshop on Radiation Hardness of Plastic Scintillator, Mar. 19–20, Tallahassee, Fla., pp. 15–28 (1990).
Zorn, Proceedings of the Workshop on Radiation Hardness of Plastic Scintillator, Mar. 19–21, Tallahassee, Fla., pp. 1–14 (1990).
Orlando et al., Chem. Communications (1971) 1551–1552; "Red– and Near–in frared–luminescent Benzazole Derivatives".
Mordzinski et al., Chem.Phys. Letters (1984) vol.111; No.4, 5; 383–388; "Mechanism of Excited–State Proton Transfer In Double Benzoxazole: . . . ".
Mordzinski, J. Phys. Chem. (1986) vol. 90, 1455–1458; "Kinetics of Excited–State Proton Transfer in Double Benzoxazoles: . . . ".

(List continued on next page.)

*Primary Examiner*—Philip Tucker
*Attorney, Agent, or Firm*—Breneman, Georges & Krikelis

[57] ABSTRACT

A new class of proton transfer, benzazole, fluorescent compounds is composed of a 2-benzazolyl moiety covalently bonded to an aromatic fused ring heterocyclic moiety. The 2-benzazolyl moiety may be a 2-benzoxazolyl, 2-benzothiazolyl, or 2-benzimidazolyl. The aromatic fused ring heterocyclic moiety may be a 3-dibenzofuranyl or 3-dibenzothiophenyl each substituted at the 2 position with a proton donating group, or a 2-carbazolyl substituted at the 3 position with a proton donating group. The proton donating group may be hydroxy, sulfonamido, carbonamido, and the like, and preferably is hydroxy. The fluors are soluble in organic matrix materials such as solvents, monomers, resins, polymers, and the like. The UV-excited fluors emit short-lived fluorescence at ≧520 nm and may be used in the manufacture of fluorescent coatings, objects, scintillators, light sources and the like. The fluors are particularly useful for radiation-hard, solid scintillators for the detection and measurement of high energy particles and radiation and for UV filter materials.

21 Claims, 4 Drawing Sheets

OTHER PUBLICATIONS

Mordzinski et al, J. Phys Chem. (1986) vol. 90; 5503–5506; "Excited–State Proton–Transfer Reactions in 2–(2'–hydroxyphenyl)benzoxazole . . . ".

Routier et al., J. Chem. Soc. (1956) 4276 "Oxygen Heterocycles. Part VI. Orientation in Substitution of 2 Methoxy-dibenzofuran".

Hori et al., Chem. Pharm. Bull. Japan, vol.22;1711–1720 (1974); "Dibenzothiophenes and Related Compounds. II. Reactions of . . . ".

Studer et al., J.Am.Chem. Soc. (1989) vol. 111; 7643–7644; "Time–Resolved Study of Photooxygenation of 3–Hydroxy-flavone".

Acheson et al., J.Chem. Soc. (1978) 1117; "The Synthesis, Reactions, and Spectra of 1–Acetoxy–, 1–Hydroxy–, and 1–Methoxy–indoles".

Sytnik et al., Radiat. Phys. Chem. (1993) vol. 41, No. 1/2, 331–349; "Spectroscopic Criteria For Wavelength Shifting, Fast, and Infrared . . . ".

Pla–Dalmau et al., Proceedings Intl. Mtg. Materials Res. Soc., 4–8 Apr. (1994), San Francisco; "Flourescent Compounds for Plastic Scintill . . . ".

Jaffe et al., "Theory & Applications of Ultraviolet Spectroscopy", John Wiley & Sons, New York, 1962; p. 431.

Molecular Probes Trade Literature: pp. 7–8, "ELF—A New Fluorogenic Phosphatase Substrate"; pp. 15–16, A New Signal Amplification . . . , (1993).

↓ HBr, HOAc

↓ PPA, 200°

BENZAZOLE COMPOUNDS WITH ESIPT FLUORESCENCE

BACKGROUND OF THE INVENTION

1. Field of the Invention

This invention relates to large Stokes shift fluorescent materials which fluoresce in the visible radiation spectrum. More particularly, this invention relates to improved organic scintillator systems useful for detecting high energy particles and electromagnetic radiation.

2. Description of Related Art

Bis-benzazoles connected through a central phenylene group have been used as fluorescent whitening or brightening agents, for instance as disclosed in U.S. Pat. Nos. 2,737,516; 3,293,258 and 3,575,996. In particular, bis-benzoxazoles are disclosed containing a central phenylene group which may be substituted with lower alkyl groups or halogen atoms.

U.S. Pat. No. 3,314,894 discloses the use of bis-benzoxazolyl compounds in scintillators. This patent discloses that the compound must be free of ionizable or dissociable units, such as —OH groups or the —NH groups of imidazole compounds.

Bis-benzazolyl hydroquinones and their alkoxy, alkylcarbonyl, lower alkyloxycarbonyl, benzoyl and phenoxycarbonyl derivatives are disclosed in Orlando et al., U.S. Pat. No. 3,673,202 in which it is disclosed that the compounds fluoresce in the visible and near-infrared regions of the spectrum when exposed to ultraviolet light. The compounds are photochemically and thermally stable and can be dissolved in organic solvents. Referring to the hydrogen substitution on the hydroquinone moiety, i.e., "R", Orlando et al. indicate that when the R substituents are other than hydrogen, they increase the solubility of the compounds in organic solvents. The compounds can be incorporated in various polymers which can be used to produce films, molded objects, or applied as coatings on ultraviolet lamps to produce various colored lights when energized. In a publication (Chemical Communications, 1971, Pages 1551–1552) entitled "Red- and Near-infrared-luminescent Benzazole Derivatives", Orlando et al. compare the luminescent properties of 2-(2-hydroxyphenyl)benzazoles to those of bis-2,5-(2-benzazolyl)hydroquinones and their methyl ether derivatives wherein the benzazole moiety is benzothiazole, benzoxazole, and benzimidazole. The ultraviolet spectra of the bis-benzazolylhydroquinones in dimethylformamide was reported to have intense absorption from 320 to 410 nm (epsilon 26,000 to 43,000). From luminescence determined in the solid state, they observed that ultraviolet stimulated luminescence of the bis unsubstituted compounds was in the red and near infrared, and when substituted with methyl a hypsochromic shift of the emission band occurred. In comparison, they noted that the unsubstituted hydroxyphenylbenzazoles emitted in the blue end of the visible region and that the replacement of the o-hydroxy group by an o-methoxy group renders these benzazoles non-luminescent. In neither reference did Orlando et al. report or suggest that the bis-2,5-(2-benzazolyl)hydroquinones are soluble in styrene, vinyltoluene, xylene, or other such high efficiency scintillator solvents, or that the fluorescence quantum yield was substantial in solution.

Mordzinski et al. have investigated excited-state proton-transfer reactions in 2-(2"-hydroxyphenyl)benzoxazole (J.Phys.Chem., 1986, 90, 5503–5506), in 2,5-bis(2-benzoxazolyl)hydroquinone (Chemical Physics Letters 1984, 111, No. 4,5; 383–388), and 2,5-bis(2-benzoxazolyl)-4-methoxyphenol (J.Phys.Chem. 1986, 90, 1455–1458). In the latter study, Mordzinski et al. indicates that 2,5-bis(2-benzoxazolyl)hydroquinone dissolved in 2-methyl tetrahydrofuran has an extinction coefficient of about 20,000 at about 24,000 cm$^{-1}$ (417 nm) and that 2,5-bis(2-benzoxazolyl)-4-methoxyphenol has an extinction coefficient of about 25,000 at about 27,000 cm$^{-1}$ (370 nm). Also in the latter study, Mordzinski et al. reported that 2,5-bis(2-benzoxazolyl)-4-methoxyphenol exhibits dual luminescence arising from primarily excited and proton-transferred species and that from temperature studies of relative fluorescent quantum yields (from 300° to 12° K.), they concluded that excited-state intramolecular proton transfer (hereinafter identified as ESIPT) was found to occur effectively at 77° K.

A number of plastic scintillators have been developed for the detection of high energy particles and radiation. Such plastic scintillators typically are comprised of a polymeric matrix, e.g., poly(vinyltoluene) (PVT) and a fluor (fluorescent compound), e.g., 3-hydroxyflavone (3-HF). Portions of such scintillators are expected to withstand radiation levels in excess of $10^4$ to $10^5$ Gy/yr without degradation of scintillator performance. Standard commercial plastic scintillators are known to suffer significant changes in performance at such radiation levels, typically due to formation of yellow to brown coloration in the matrix which absorbs substantial luminescence in the blue to UV spectral region. Attempts to restore the performance of radiation discolored plastic scintillators by treatments, such as by annealing or with oxygen, have only met with limited success. The issue of "radiation hardness" of plastic scintillators was the subject of a workshop on Mar. 19–21, 1990. (See *Proceedings of the Workshop on Radiation Hardness of Plastic Scintillator*; Mar. 19–20, 1990; Florida State University, Tallahassee, Fla.; Editor, Kurtis F. Johnson.) In these Proceedings, Clough et al., Pages 15–28, discusses radiation effects on scintillating fiber optics for the Super-conducting Super Collider (SSC); Zorn, Pages 1–14 discusses the design of a radiation-hard plastic scintillator for high luminosity HADRON colliders; and Kasha et al., Pages 49–60, discusses the molecular electronic criteria for the selection of radiation-hard scintillators each of which is included herein by reference. U.S. Pat. No. 4,594,179 discloses a method of reducing reabsorption effects in scintillators by using solutes with large Stokes shifts, i.e., a large shift towards the red in the emitted luminescence from the region of the absorbed radiation. 3-hydroxyflavone (3-HF) is proposed as such a solute in a scintillator matrix such as poly(vinyltoluene) (PVT).

Recently a class of proton transfer, bis-benzazole, fluorescent compounds and their use in scintillator detectors has been disclosed by Kauffman, U.S. Pat. No. 5,298,189. These fluors include substituted or unsubstituted 1,4-bis(2-benzazolyl)-2-hydroxybenzenes and 1,4-bis(2-benzazolyl)-2-amidobenzenes wherein the benzazolyl group may be benzoxazolyl, benzimidazolyl, and benzothiazolyl. The disclosed uses for these fluors include the manufacture of fluorescent coatings, objects, scintillators, and light sources. The fluors are disclosed to be particularly useful for radiation-hard, solid scintillators for the detection and measurement of high energy particles and radiation.

Although advances have been made to produce a radiation hard scintillator, there still exists a need to produce radiation hard fluors which are characterized by: a very high extinction coefficient in the near ultraviolet; a very large Stokes shifted fluorescence emission which is free of phosphorescence emission and is spectrally matched to the sensitivity of photodetection systems used; a high fluorescence efficiency at room temperature; a short fluorescence lifetime to provide fast system response times; and substantially no self-absorption of the emitted fluorescence by the fluor. Moreover, there still exists a need for a fluor that is soluble in the polymeric matrix as well as the monomer precursors thereto; is substantially stable during addition polymerization of the polymeric matrix and during prolonged exposure to high energy radiation; and is photochemically stable and resistant to ambient oxidation.

SUMMARY OF THE INVENTION

These needs are met by the fluor of this invention which is an organic, fluorescent material comprising a 2-benzazolyl compound having the structure:

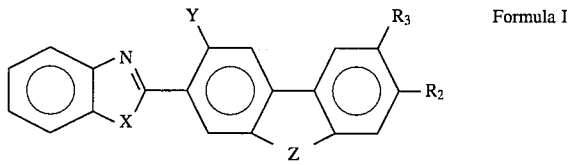

Formula I wherein X is a —N($R_1$)— group, —O—, or —S—; Y is a proton donating group; Z is a —N($R_1$)— group, —O—, or —S—; $R_1$ is a H or a $C_1$ to $C_{10}$ alkyl group; $R_2$ is a H or an added 2-benzazolyl group; $R_3$, is a H when $R_2$ is a H and $R_3$ may be a Y when $R_2$ is an added 2-benzazolyl group; and the 2-benzazolyl and/or the added 2-benzazolyl is substituted or unsubstituted. In one embodiment of this invention, the organic, fluorescent material is used in scintillator devices to detect high energy particles and electromagnetic radiation such as γ, α, β, neutrons, and the like. In a second embodiment of this invention, the organic, fluorescent material is used in UV filter materials and devices such as eyeglass lenses and the like.

An added embodiment of this invention is a fluorogenic alkaline phosphatase substrate material comprising a 2-benzazolyl compound having the structure:

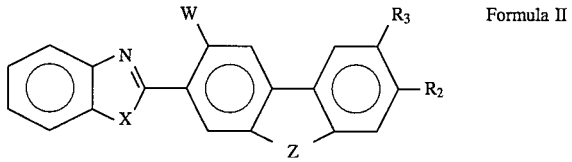

Formula II wherein X is a —N($R_1$)— group, —O—, or —S—; W is an alkaline phosphate ester disalt of an ammonium, sodium or potassium ion; Z is a —N($R_1$)— group, —O—, or —S—; $R_1$ is a H or a $C_1$ to $C_{10}$ alkyl group; $R_2$ is a H or an added 2-benzazolyl group; $R_3$ is a H when $R_2$ is a H and $R_3$ may be a W when $R_2$ is an added 2-benzazolyl group; and the 2-benzazolyl and/or the added 2-benzazolyl is substituted or unsubstituted. In particular the W disalt anion is —O—($PO_3$)$^{2-}$. In this embodiment, the alkaline phosphatase substrate material of this invention is used for immunohistochemical applications to detect sites of phosphatase enzyme activity.

BRIEF DESCRIPTION OF THE DRAWINGS

The invention can be more fully understood from the following description thereof in connection with the accompanying drawings described as follows.

Throughout the following detailed description, similar reference characters refer to similar elements in all figures of the drawings.

DETAILED DESCRIPTION OF THE INVENTION

Figure 1:
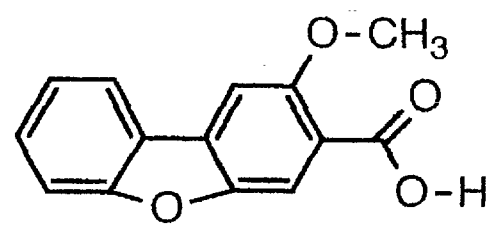
FIG. 1 illustrates a method for synthesizing a 3-(2-benzoxazolyl)-dibenzofuran compound of this invention.
Figure 1:
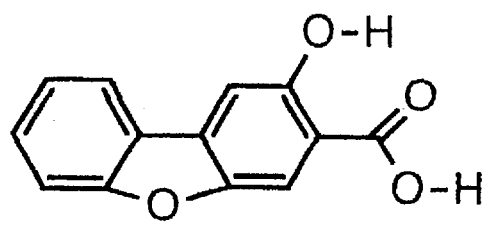
Figure 1:
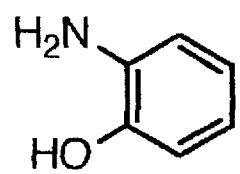
Figure 1:
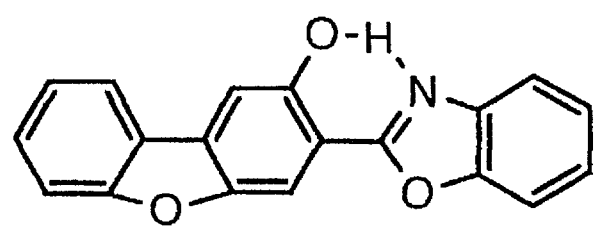

The present invention relates to a novel organic, fluorescent material and alkaline phosphate ester disalt precursors thereof. The organic, fluorescent material of this invention, comprises a 2-benzazolyl compound and optionally a matrix material in which the compound is dispersed. The novel organic, fluorescent material of this invention preferably comprises a matrix material, such as a solvent, a liquid monomer, a transparent solid polymer, and the like, having dispersed therein a specific class of ESIPT 2-benzazole fluors, i.e., organic fluorescent compounds. This new class of 2-benzazole fluors possesses unusually high extinction coefficients in the near ultraviolet spectral region, i.e., about 37,000 or greater at about 420 nm or shorter and unusually high fluorescence efficiency at room temperature in the visible spectral region of about 520 nm or longer, preferably 540 nm or longer, i.e., a fluorescence quantum yield of about 0.3 or greater along with a fast response time, i.e., a fluorescence lifetime of 10 nanoseconds or less and preferably 5 nanoseconds or less. The fluors of this invention are substantially free of reabsorption of the Stokes shifted fluorescence and the fluorescence emission spectra overlaps the most transparent portion of the matrix materials as well as the highly sensitive regions of green extended photomultiplier tubes, i.e., between about 480 and 600 nm. Thus, solutions of the fluors of this invention are substantially clear and colorless unless stimulated by near ultraviolet radiation to produce the visible, e.g., green to orange, fluorescence. The fluors are readily soluble in organic solvents, liquid monomers, and polymeric matrix materials, and are substantially stable during polymerization of the monomer to a polymeric matrix as well as during their use in scintillation detectors for detection of high energy particle beams and high energy radiation or their use in UV filter materials such as sunglasses and the like. The organic, fluorescent materials of this invention, may also be used in UV-only fluorescent pigments. Such pigments may be used in printing inks, in fluorescent mineral displays, as well as in currency and other documents to prevent counterfeiting.

The novel, 2-benzazole fluors of this invention have the structure defined by Formula I defined supra, and are comprised of a 2-benzazolyl moiety covalently bonded to an aromatic fused ring heterocyclic moiety. The 2-benzazolyl moiety may be 2-benzoxazolyl, 2-benzothiazolyl, or 2-benzimidazolyl. The aromatic fused ring heterocyclic moiety may be a 3-dibenzofuranyl or 3-dibenzothiophenyl each substituted at the 2 position with a proton donating group, or a 2-carbazolyl substituted at the 3 position with a proton donating group. The proton donating group may be hydroxy, sulfonamido, carbonamido, and the like, and preferably is hydroxy. Optionally the aromatic fused ring heterocyclic moiety may be substituted at the 6 position with a second 2-benzazolyl moiety. Optionally the 2-benzazolyl group may be substituted in the 4, 5, 6, and/or 7 positions with one or more functional groups. In a preferred embodiment of this invention the 2-benzazolyl compound has the structure:

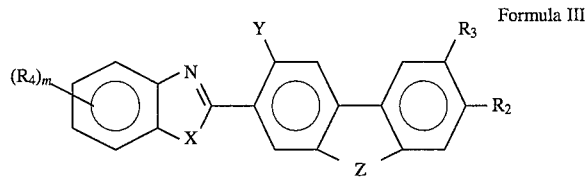

Formula III wherein X is a —N(R$_1$)— group, —O—, or —S—; Y is a proton donating group, with the proviso that when X is a —N(R$_1$)— group, then Y may be an amido group; Z is a —N(R$_1$)— group, —O—, or —S—; R$_1$ is a H or a C$_1$ to C$_{10}$ alkyl group; R$_2$ is a H or an added 2-benzazolyl group; R$_3$ is a H when R$_2$ is a H and R$_3$ may be a W when R$_2$ is an added 2-benzazolyl group; R$_4$ is a C$_1$ to C$_{10}$ alkyl group or aryl group; and m is 0 or an integer from 1 to 4. In a more preferred embodiment of this invention, X is a —N(R$_1$)— group, —O—, or —S—; Y is a hydroxy group or a sulfonamido group of the structure: —NH—SO$_2$—R$_5$ wherein R$_5$ is a C$_1$ to C$_{10}$ alkyl group or aryl group, with the proviso that when X is a —N(R$_1$)— group, then the amido group, Y, may be a sulfonamido group of the structure: —NH—SO$_2$—R$_5$; and R$_4$ is a C$_1$ to C$_6$ alkyl group or a phenyl or aro group; m is 0, 1, or 2; R$_2$ is H and R$_3$, is H. Still more preferably, R$_1$ is a H or a methyl, ethyl, propyl, or butyl group; R$_2$ and R$_3$ are H; R$_4$ is a methyl, ethyl, propyl, butyl, or phenyl group; and R$_5$ is a methyl, ethyl, propyl, butyl, benzyl or toluyl group. Also useful are substituted benzazolyl groups wherein R$_4$ is a perfluorinated C$_1$ to C$_{10}$ alkyl group, e.g. such as trifluoromethyl, or other such equivalent electron withdrawing group, such as chloro or alkylsulfonyl.

Preferred 2-benzazolyl compounds include the novel 2-benzoxazolyl compounds wherein the aromatic fused ring heterocyclic moiety is a 2-hydroxy-3-dibenzofuranyl group, a 2-hydroxy-3-dibenzothiopheneyl group, or a 2-hydroxy-3-carbazolyl group which may be substituted with one or more methyl, ethyl, propyl, butyl or phenyl group(s). Particularly preferred of this class are 3-(9,9-dipropylindeno[3,2-f]benzoxazol-2-yl)-2-hydroxydibenzofuran, 3-(5-chloro-2-benzoxazolyl)-2-hydroxydibenzofuran, 2-hydroxy-3-(5-phenyl-2-benzoxazolyl)dibenzofuran, 2-hydroxy-3-(6-methyl-2-benzoxazolyl)dibenzothiophene, 2-hydroxy-3-(6-methyl-2-benzoxazolyl)dibenzofuran, 2-hydroxy-3-(5-methyl-2-benzoxazolyl)dibenzofuran, 2-hydroxy-3-(2-benzoxazolyl)dibenzofuran, 9-ethyl-3-hydroxy-2-(6'-methyl-2-benzoxazolyl)carbazole, 2-(9,9-dipropylindeno[3,2-f]-2-benzoxazolyl)-9-ethyl-3-hydroxycarbazole, and the like.

Figure 2:
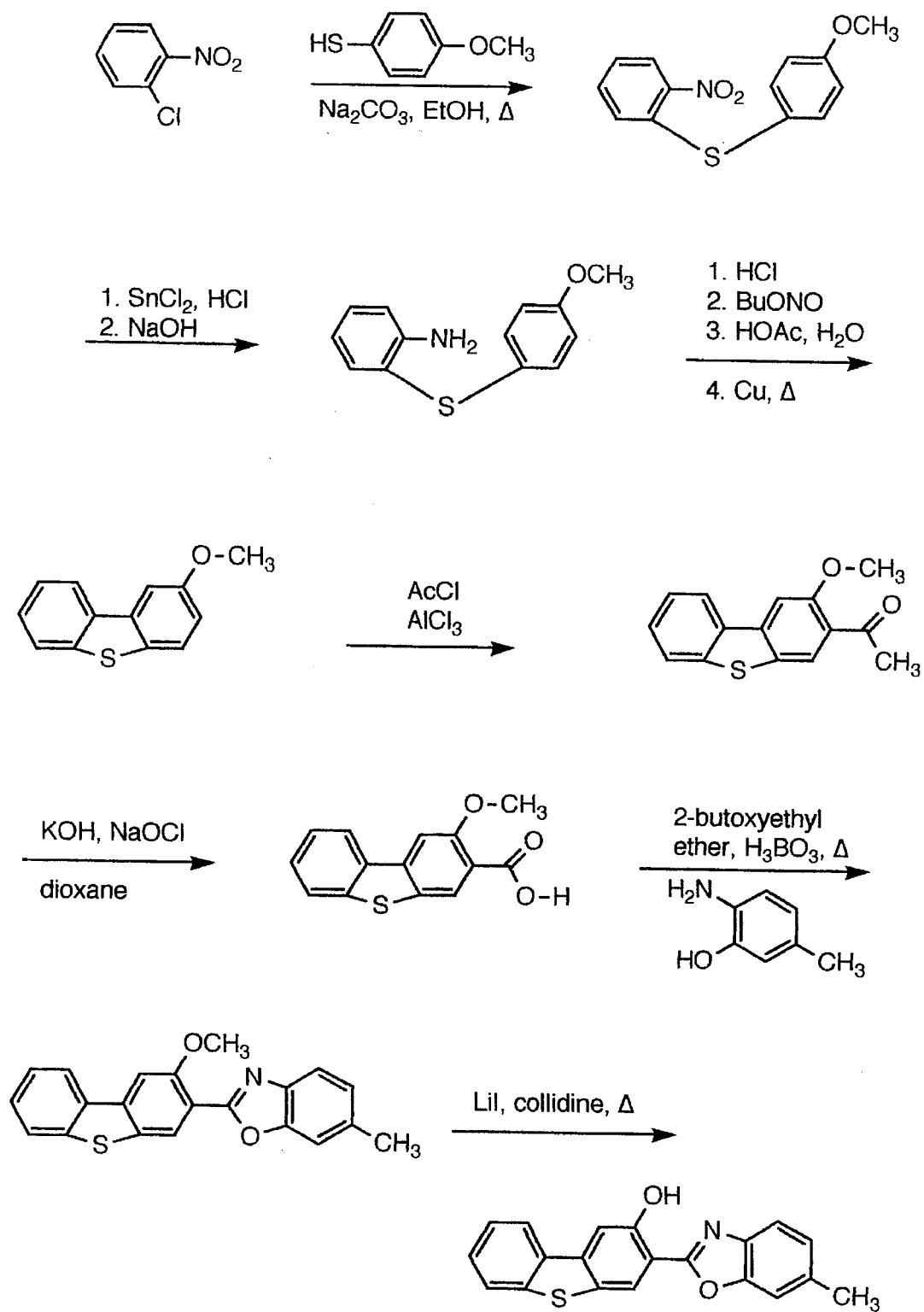
FIG. 2 illustrates a method for synthesizing a 3-(2-benzoxazolyl)-dibenzothiophene compound of this invention.
Figure 3:
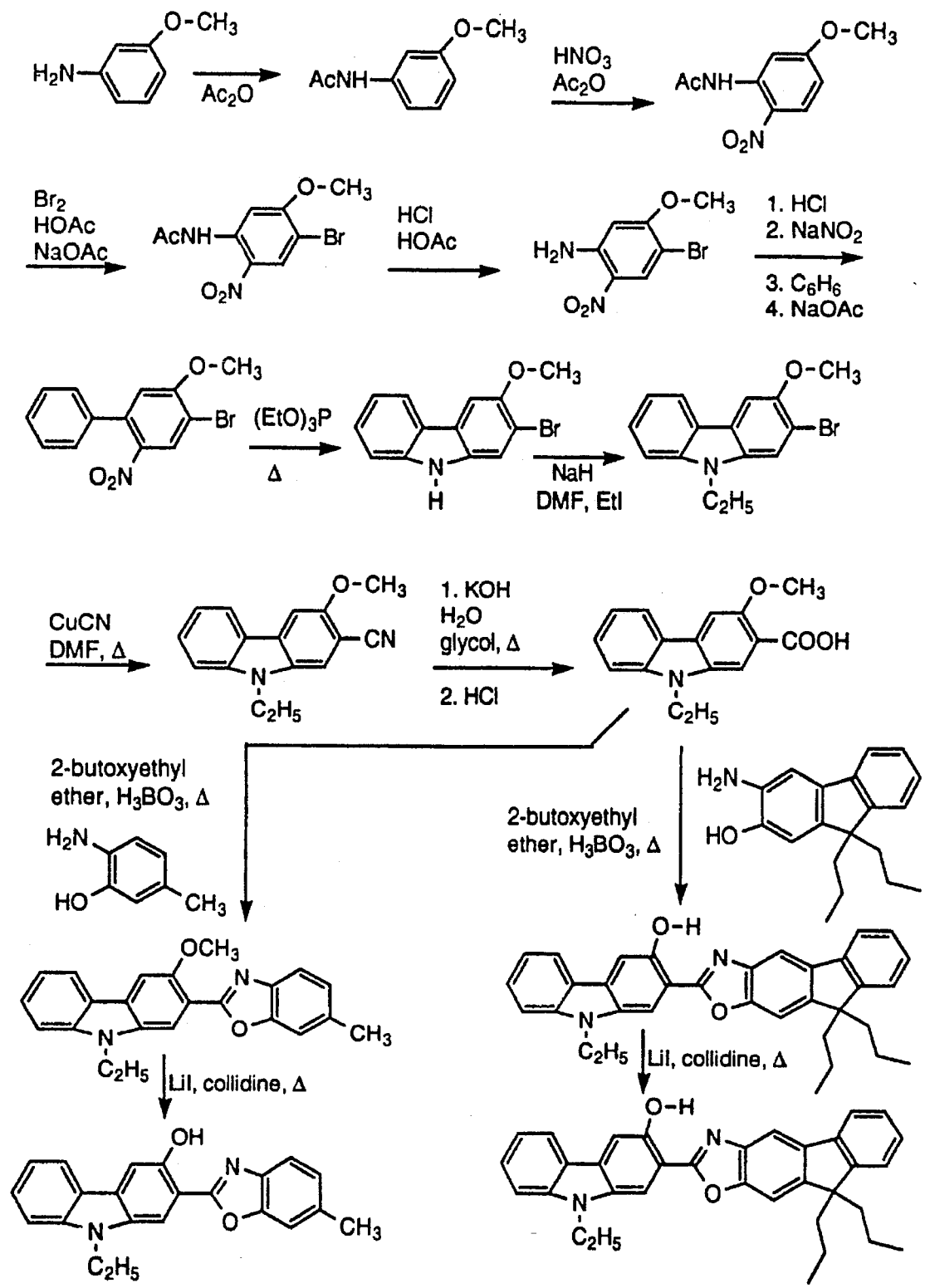
FIG. 3 illustrates a method for synthesizing 3-(2-benzoxazolyl)-carbazole compounds of this invention.

The 2-benzazolyl compounds of this invention typically may be prepared by conventional organic synthesis methods, although in specific instances unique procedures may be devised. In general, the 2-benzazolyl compounds of this invention may be prepared using synthesis procedures disclosed by Kauffman, U.S. Pat. No. 5,298,189, by Mordzinski et al. in Chemical Physics Letters 1984, 111, No. 4,5; 383–388, and by Orlando et al. U.S. Pat. No. 3,673,202, each of which is included herein by reference. Preferred synthesis methods are illustrated in the examples that follow. In particular, FIG. 1 illustrates a preferred method of synthesizing a 3-(2-benzoxazolyl)dibenzofuran compound of this invention and is described in detail in Example 1; FIG. 2 illustrates a preferred method of synthesizing a 3-(2-benzoxazolyl)dibenzothiophene compound of this invention and is described in detail in Example 4; and FIG. 3 illustrates a preferred method of synthesizing 2-(2-benzoxazolyl)carbazole compounds of this invention and is described in detail in Examples 10 and 11, each of which follows.

It has been found that the acidity of the proton transfer group influences the efficiency of proton transfer fluorescence of the 2-benzazole fluors of this invention. Typically, the group Y is a proton transfer group having a pK$_a$ between about 5 and about 15, with the proviso that when X is a —NR$_1$— group, then Y is a hydroxy or an amido group and preferably a sulfonamido group. Such proton transfer groups include hydroxy, sulfonamido, carbonamido, and the like.

Solutions of the ESIPT 2-benzazole fluors of this invention, absorb strongly in the ultraviolet to blue spectral region, i.e., about 420 nm or shorter (preferably between 300 and 420 nm), with absorption maxima in the ultraviolet indicating an extinction coefficient of about 37,000 or greater is typical for these fluors. These 2-benzazole fluors likewise possess unusually strong, ultraviolet-stimulated, proton-transfer fluorescence in the visible spectral region, having a fluorescence emission peak of about 520 nm or longer at room temperature or higher, and preferably between 520 nm and 800 nm, (strong fluorescence has been observed at temperatures of 400° K. and above) indicating that a fluorescence quantum yield of about 0.3 or greater, preferably 0.5 or greater at 300° K. can be achieved. When the compositions of this invention are used as a scintillator, high light output, i.e., high scintillator efficiency, translates to a fluor with both a good ability to absorb light (high extinction coefficient, ε) and high fluorescence quantum yield, Φ. The fluorescence lifetimes of the fluors used in the materials of this invention have a fluorescence life time of about 10 nanoseconds or less and preferably 5 nanoseconds or less, which insures a fast response time (i.e., scintillation decay time) when used in a scintillator system with minimum dead time during which the fluor is present in its excited state. Such fast response times of 10 nanoseconds or less are correlated to the fluors' high extinction coefficients of 37,000 or greater in the near ultraviolet spectral region. Furthermore, there appears to be substantially no self absorption of the stimulated visible fluorescence by these 2-benzazole fluors. In addition the matrix material typically is substantially transparent in this portion of the visible spectral region. Accordingly, an organic fluorescent material of this invention is substantially transparent to its own fluorescent emission within the visible spectral region which enhances its use as a radiation hard scintillator material. The extinction coefficient(s), fluorescence quantum yield and fluorescence life time of a particular fluor may be determined by conventional means, e.g., such as disclosed in Harrah et al., U.S. Pat. No. 4,594,179 which is incorporated herein by reference. The particular means used to determine extinction coefficients, fluorescence efficiencies and quantum yields in this invention are illustrated in the examples to follow.

The matrix material in which the ESIPT, 2-benzazolyl compounds are dispersed may be any vehicle suited to the particular application for the organic, fluorescent materials of this invention. Typically, the matrix material is an organic solvent for the fluor, a polymerizable monomer, a polymeric material, or any combination thereof, e.g., such as polymerizable coating solution of the fluor. For efficient use with the fluor of this invention, the matrix material should be transparent in at least a portion of the visible electromagnetic spectrum and preferably in the visible spectral region of about 520 nm or longer. The matrix material should be capable of completely dispersing the fluors of this invention to produce an optically clear fluorescent composition substantially free of macro size particles which would scatter incident radiation. Preferably, the fluor is completely dissolved in the matrix material to form a homogeneous solution.

The matrix material may be chosen from any conventional organic solvent for 2-benzazolyl type compounds. Illustrative of such solvents are toluene, xylene, phenylcyclohexane, p-dioxane, alkanols, glycols, alkoxyalkanols, phenoxyalkanols, N,N-dimethyl-acetamide and the like, of which xylene, toluene and lower alkanols are preferred. An unusual feature of the fluors of this invention is that ESIPT fluorescence is not substantially affected by the use of alkanols and even small amounts of water as contrasted to such conventional fluors. Accordingly, although organic solvents typically are used as matrix materials, semiaqueous solvents may also be used provided they do not adversely affect fluorescence efficiency of the dispersed fluor. Illustrative of useful semiaqueous solvents are mixtures of water with miscible alkanols, glycols, alkoxyalkanols, phenoxyalkanols and the like.

The matrix material may be a solid polymeric material formed by free radical or condensation polymerization. Illustrative of such polymeric materials are vinyl, styryl, acrylic, and diene polymers and copolymers thereof, and polyesters, polyamides, polyimides, polycarbonates, and the like. Preferred polymeric matrix materials for use in plastic scintillators are styrene and vinyl-toluene. Preferred polymeric matrix materials for use in UV filters and lenses include polycarbonate and polymethyl methacrylate. It is a characteristic of the 2-benzazolyl compounds of this invention that they possess excellent solubility in polymeric matrices providing intense visible fluorescence to the polymer composition. Preferably the fluor should possess adequate solubility in polystyrene or other organic polymers so that the fluor may be used in a scintillator as a primary fluor or as a "waveshifter" secondary fluor. When used as a primary fluor, i.e., without a secondary fluor, the concentration in the polymeric matrix should be about $10^{-2}$M or greater, and when used as a "waveshifter" the concentration should be about $10^{-4}$M or greater.

The 2-benzazolyl compounds of this invention may be dispersed in the polymeric matrix by any conventional method depending on the end use of the resulting fluorescent composition formed. Thus, the fluor and the polymer may be dissolved in a cosolvent therefor and applied to a substrate and dried to form an adherent polymeric coating. The fluor may also be blended in melted polymer, e.g., polystyrene, polycarbonate and the like, and then extruded or cast into any desired shape, e.g., into a film, a rod, a disc, and the like. The fluor may also be dissolved in the monomeric prepolymer composition which is then polymerized to form a solid polymer solution of the 2-benzazolyl compound. A polymerizable composition comprises one or more polymerizable component(s) and a 2-benzazolyl compound having the structure of Formula I. In a preferred embodiment of this invention, the polymerizable component(s) is a free radical, addition polymerizable monomer having one or more terminal, ethylenically unsaturated groups. Preferred free radical, addition polymerizable monomers are taken from the group consisting of styrene, vinyltoluene, $C_2$ to $C_{20}$ alkyl styrene, divinylbenzene, methyl methacrylate and mixtures thereof. The 2-benzazolyl compounds of this invention have the advantage that they are soluble in both the polymerizable components as well as the polymerized matrix in highly effective amounts. In addition, the 2-benzazolyl compounds of this invention are substantially unaffected by the polymerization process (in contrast to conventional fluors, such as 3-HF, which exhibit thermal instability at the high temperatures used for the thermal polymerization process). The actual concentration in a polymerizable composition will depend on the particular fluor used, as well as the particular utility of the resulting fluorescent, polymerized composition. Illustrative of concentration differences is the use of a particular fluor in a plastic scintillator either as a primary fluor in which case the concentration may be 1% by weight or more, or as a secondary fluor in which case the concentration may be 0.1% or less.

The organic, fluorescent materials of this invention which include a matrix material are particularly useful for radiation-hard, plastic scintillator devices which are used to detect high energy particles and photons. For the purpose of this invention, the term "radiation-hard" is intended to mean that the detection efficiency of the scintillator device, or its components, has a substantially stable high detection efficiency over a prolonged period of irradiation by high energy particles or photons, e.g., the detection efficiency changes by no more than 20% during an exposure to high energy radiation of $10^5$ Gy/yr or to 10 megarads of $^{60}$Co γ-rays. For the purpose of this invention, rad-hardness is intended to mean that there is minimal drop in scintillator light output when it is subjected to 10 megarads or more of $^{60}$Co γ-rays. Methods of making and using conventional scintillators are disclosed in Harrah et al., supra, as well as the patents and publications cited therein, and include considerations such as conventional selection of primary matrix constituents, compounds for use as the various solutes, the number of solutes to be employed, the concentrations of various solutes, the fabrication of the scintillators themselves, their use in various conventional optical/radiometric systems, etc. Likewise, considerations of scintillator performance and optimization are disclosed in *Proceedings of the Workshop on Radiation Hardness of Plastic Scintillator*; Mar. 19–20, 1990; Florida State University, Tallahassee, Fla.; Editor, Kurtis F. Johnson, wherein the treatment of radiation deteriorated plastic scintillators by annealing or with oxygen is discussed to help restore original performance. The radiation-hard fluors of this invention may be used with these conventional practices to produce radiation-hard scintillators with improved detection efficiency. Most notably, the polymerizable compositions of this invention discussed supra are particularly useful in forming radiation-hard scintillators by methods such as described in Harrah et al. and the *"Proceedings"*, supra.

A radiation hard plastic scintillator comprises a polymeric matrix material, preferably an aromatic polymeric material, and at least one 2-benzazolyl compound having the structure of Formula I, defined supra.

The polymeric matrix material typically is one or more aromatic polymer(s), such as polystyrene, polyvinyltoluene, and the like, or is a copolymer of styrene and/or vinyltoluene with $C_2$ to $C_{20}$ alkyl styrene, divinylbenzene, and the like. Alternatively, the polymeric matrix material may be an acrylic polymer having dissolved therein an aromatic compound, e.g., such as poly(methyl methacrylate) containing 5 to 25% by weight of naphthalene dissolved therein. When the plastic scintillator is used in the form of a fiber, it must possess sufficient flexibility to be bent around sharp radius turns and it should have a sufficiently low glass transition temperature so that any stress in the fiber may be removed by annealing. Typically, such polymeric materials should possess a glass transition temperature (Tg) of about 70° C. or lower, and preferably between about 40° C. and 70° C. Low Tg siloxane elastomers may also be used. Flexibility may be imparted to the polymeric material by conventional methods provided that scintillator characteristics are not adversely affected. Such methods include the use of plasticizers, copolymer components substituted with a long alkyl chain, e.g., decylstyrene, or combinations thereof.

In addition to the properties described supra, the 2-benzazolyl compounds of this invention are substantially photochemically stable, are stable to ambient oxidation and are substantially radiation hard particularly when used in the plastic scintillators of this invention. The term "photochemically stable" is intended to mean that the 2-benzazolyl compounds of this invention do not decompose or interact with other fluors or matrix materials as a result of exposure to ultraviolet radiation of the type and levels characteristic of use in a plastic scintillator detector, UV filters and lenses, or the like. The term "stable to ambient oxidation" is intended to mean that the 2-benzazolyl compounds of this invention do not oxidize in the presence of ambient oxygen or other oxidants at levels characteristic of use in a plastic scintillator detector or its treatment. The term "radiation hard fluor" is intended to mean that the fluorescence of a 2-benzazolyl compound of this invention is substantially unchanged during an exposure to high energy radiation of $10^5$ Gy/yr, so that the detection efficiency of a polystyrene scintillator containing only the 2-benzazolyl compound changes by no more than 20%. The radiation hard plastic scintillators of this invention may be made by dissolving a 2-benzazolyl compound of Formula I, with the addition of a primary scintillator such as p-terphenyl, in liquid monomer or prepolymer composition, e.g., styrene, vinyltoluene; casting the fluor/monomer solution into a mold of desired shape; and then polymerizing the monomer to form a polymer solution of the fluor. After polymerization the molded polymer solution may be further shaped, polished or otherwise treated to form the plastic scintillator of this invention. Methods of making and testing the plastic scintillators of this invention will be further illustrated in the examples that follow.

The organic, fluorescent material of this invention may be used as a UV filter material in devices such as protective eye-ware (e.g. eyeglass lenses, sunglasses, safety glasses, face shields, and the like), protective coatings, and the like. In particular, the 2-benzazolyl compounds may be dispersed in any matrix material suitable for the intended application. A significant advantage of some of the organic, fluorescent materials of this invention over conventional UV filter materials, is that the materials appear colorless to the eye, while having a UV cutoff near to, or below 400 nm, i.e., the material is substantially opaque to UV radiation. In addition, the 2-benzazolyl compounds of this invention are stable to most ambient and processing conditions as discussed supra. A typical use for a UV filter material is for protective eye-ware wherein a polymeric material containing the 2-benzazolyl compound is molded to form the lens. For this purpose any optical grade polymeric matrix material may be used such as those described supra. Preferably, optical grade polycarbonate resin containing about 0.25%, or less, by weight of the 2-benzazolyl compound is used to form a lens blank by conventional injection molding. Such a lens forming process is illustrated in Example 9 which follows. Protection from UV radiation may be provided by coatings of some of the organic, fluorescent materials of this invention. The coatings may be solid, semi-solid or liquid and may be applied to an object as either a permanent or temporary coating. The object itself may need protection from UV radiation, e.g., a photograph or other photosensitive surface, or the coated object may provide UV protection to another object, e.g., a coated preformed lens or face-shield for use as eye-ware, coated windows, and the like.

In an added embodiment of this invention, a fluorogenic alkaline phosphatase substrate material containing a 2-benzazolyl compound having the structure of Formula II is used for immunohistochemical applications to detect sites of phosphatase activity. The 2-benzazolyl compound of Formula II, is substantially the same as that of Formula I which is described supra, with the exception that Formula II contains an alkaline phosphate ester disalt (i.e., $—O—(PO_3)^{2-}$) of an ammonium, sodium or potassium ion (W) in place of the proton donating group (Y) of Formula I. It is a characteristic of the 2-benzazolyl compound of Formula II that enzyme activity can convert the alkaline phosphate ester salt (W) to a hydroxy group (Y), thereby converting the compound of Formula II into a 2-benzazolyl compound of Formula I having ESIPT fluorescence. Illustrative of 2-benzazolyl compound of Formula II are the hydroxy compounds listed supra, wherein the hydroxy moiety has been replaced by the phosphate ester disalt moiety. In addition to the 2-benzazolyl compound of Formula II the alkaline phosphate substrate material comprises an aqueous alkaline solution in which the 2-benzazolyl compound is soluble therein. In the practice of this invention, the soluble 2-benzazolyl compound fluoresces only weakly in the blue region when irradiated with UV light. But, upon enzymatic cleavage wherein the phosphate is enzymatically removed, the insoluble, hydroxy-2-benzazolyl compound of Formula I is precipitated at the site of the enzymatic activity. The intense ESIPT fluorescence of the precipitate is in the yellow-green portion of the visible spectrum and is separated from the UV excitation by more than 100 nm. Since the difference between the excitation and emission maxima of most endogenous fluorescent components, the ESIPT fluorescence signal is clearly distinguishable from the inherent autofluorescence sometimes seen in cells and tissue. Thus the alkaline phosphate substrate material of this invention may be used as a fluorogenic phosphatase substrate in commercially available systems such as the ELF™ Immunohistochemistry Kits marketed by Molecular Probes, Eugene, Oreg.

This invention will now be illustrated by the following examples but is not intended to be limited thereby. Unless otherwise indicated, temperature is given in degrees (°) Centigrade and metric units are used.

EXAMPLE 1

The fluor 2-hydroxy-3-(2-benzoxazolyl)-dibenzofuran, referred to herein after as Oxazole 545, was prepared according to the synthesis illustrated in FIG. 1 as follows.

A mixture of 2-methoxydibenzofuran-3-carboxylic acid 21.62 g, (prepared by the method disclosed in Cl. Routier, Ng. Ph. Buu-Hoï, and R. Royer, J. Chem. Soc., 4276 [1956] which is incorporated herein by reference), 48% hydrobromic acid (250 ml) and acetic acid (175 ml) was boiled under reflux, allowing bromomethane to escape, for 2 hrs, removed from the heat source, diluted with 400 ml of water with stirring, and cooled in ice to 30° C. The crystalline product was filtered, washed with water, and dried, to give 19.9 g (98%) of 2-hydroxy-dibenzofuran-3-carboxylic acid, m.p. 301°–2° dec. An analytical sample was prepared by twice recrystallizing a portion from 2-ethoxyethanol, m.p. 301°–303° dec.

PMR, 60 MHz, 5% in DMSO-$d_6$: δ=7.3–7.8 ppm from tms (4H, m, Hs on C1, C5–C7); 8.1 (1H, s, H on C4); 8.2 (1H, d, J=6 Hz, H on C8).

Anal. Calc. for $C_{13}H_8O_4$: C, 68.42; H, 3.54%. Found: C, 68.57; H, 3.58%.

The acid (4.40 g) was ground in a mortar with 2-aminophenol (2.11 g) and added to 40 ml of polyphosphoric acid at ≈100°, then held at 200° for 16 hrs, cooled to ≈100°, and quenched in a mixture of 250 g of ice and 150 g of water. The pH was lowered to 3 with 19M sodium hydroxide, and the crude product was filtered and dried to give 3.19 g of sticky solid. This was extracted from a small Soxhlet with 150 ml of toluene. The cooled extract was passed through Br. I alumina, which was further eluted with 300 ml of toluene and 400 ml of dichloromethane to give, on evaporation, a solid, which was recrystallized from 25 ml xylenes to give 0.36 g of product, m.p. 267°–70°. This product was recrystallized from 35 ml of 2-ethoxyethanol to give 0.32 g (6%) of needles, m.p. 269°–270°.

The solubility in xylenes was 1.2 g/L or $4.1 \times 10^{-3}$ M. UV absorption in toluene: $\lambda$max 318 nm ($\epsilon$=34,000), 333 nm ($\epsilon$=47,000), 358 nm ($\epsilon$=26,000), 376 nm ($\epsilon$=28,000). Fluorescence emission: $\lambda$max 545 nm, $\Phi$=0.36 in toluene.

EXAMPLE 2

To prepare the fluor 2-hydroxy-3-(5'-methyl-2-benzoxazolyl)-dibenzofuran, hereinafter referred to as Oxazole 545M5' a mixture of 2-hydroxydibenzofuran-3-carboxylic acid (4.56 g), 2-amino-4-methylphenol (2.46 g), 25 ml of 2-butoxyethyl ether, and 0.20 g of boric acid was heated at 170° overnight, then more strongly, so that half the solvent distilled during ≈2 hrs. When the residue reached 20° it was filtered, the black solid was washed with 50 ml of 2-propanol, and dried, to give 1.83 g. This product was extracted from 4 cm of Silica Gel™ under 2 cm of Br. I alumina in a small Ace-Kauffman column with 80 ml of toluene until all fluorescent material was extracted; the extract was kept at −20°, filtered, and the solid washed with 25 ml of 95% ethanol and dried to give 0.78 g of material which was recrystallized from 32 ml of 2-ethoxyethanol, yielding 0.60 g (10%) of pink needles, m.p. 248°–250°.

Anal. Calc. for $C_{20}H_{13}NO_3$: C, 76.18; H, 4.15; N, 4.44%. Found: C, 76.11; H, 4.05; N, 4.33%.

UV absorption in toluene: $\lambda$max 283 nm ($\epsilon$=9,690), 320 ($\epsilon$=26,200), 335 nm ($\epsilon$=37,400), 360 nm ($\epsilon$=22,900), 377 nm ($\epsilon$=24,800). Fluorescence emission: $\lambda$max 545 nm, $\Phi_f$=0.41 in toluene.

EXAMPLE 3

To prepare the fluor 2-hydroxy-3-(6'-methyl-2-benzoxazolyl)-dibenzofuran, hereinafter referred to as Oxazole 545M6', a mixture of 2-hydroxydibenzofuran-3-carboxylic acid (4.56 g), 2-amino-5-methylphenol (2.46 g), 25 ml of 2-butoxyethyl ether, and 0.20 g of boric acid was treated as in Example 2. The toluene extract was diluted with half its volume of methanol before cooling to −20° to obtain pink needles, 0.068 g (1.1%) m.p. 242°–242.5°.

Anal. Calc. for $C_{20}H_{13}NO_3$: C, 76.18; H, 4.15; N, 4.44%. Found: C, 75.98; H, 3.98; N, 4.31%.

UV absorption in toluene: $\lambda$max 283 nm ($\epsilon$=28,800), 304 ($\epsilon$=22,000), 319 ($\epsilon$=32,800), 335 nm ($\epsilon$=44,500), 359 nm ($\epsilon$=28,000), 378 nm ($\epsilon$=30,500). Fluorescence emission: $\lambda$max 545 nm, $\Phi_f$=0.41 in toluene.

The fluors of Examples 2 and 3 each have methyl substitution (5' and 6' respectively) on the 2-benzoxazolyl group as compared to the unsubstituted fluor of Example 1. The presence of the methyl group in either position increases $\Phi$ by 10% over the unsubstituted fluor. However, $\epsilon$ drops by 10% in the fluor of Example 2, but not in the fluor of Example 3. Since light output is proportional to fluorescence efficiency (FE), and FE=$\Phi \cdot \epsilon$, the fluor of Example 3 is 10% brighter than the fluors of Example 1 and Example 2.

EXAMPLE 4

The fluor 2-hydroxy-3-(6-methyl-2-benzoxazolyl)dibenzothiophene was prepared according to the synthesis illustrated in FIG. 2 as follows.

A solution of sodium carbonate monohydrate (27.4 g, 0.221 mole) in 100 ml of water was prepared, to which was added 4-methoxybenzenethiol (25.0 g, 0.179 mole); this dissolved in a few minutes. Then a warm solution of 1-chloro-2-nitrobenzene (28.1 g, 0.179 mole) in 125 ml of 95% ethanol was added, and the mixture was heated under reflux for 45 min, then at 80° for 20 hrs. The heat was removed, and 100 ml of water was added to dissolve salts, then the mixture was quenched in 300 ml of water. The solid was filtered, washed with water, slurried in 200 ml of methanol for 5 min., filtered, washed with methanol, and dried to give 37.3 g (80%) of 4-methoxy-2'-nitrodiphenyl sulfide, m.p. 97°–99°.

Anal. Calc. for $C_{13}H_{11}NO_3S$: C, 59.75; H, 4.24; N, 5.36%. Found: C, 59.98; H, 4.43; N, 5.36%.

Into a 3-liter flask placed 198 g of stannous chloride dihydrate and 264 ml of 12M hydrochloric acid. Stirred to obtain complete solution, then added 38.3 g of 4-methoxy-2'-nitrodiphenyl sulfide and 396 ml of acetic acid. A mild exotherm to 67°–75° was followed by deliberate heating to reflux at 89° for 20 minutes, by when the mixture became colorless. Kept overnight at 20°, cooled in ice, and added 2.5 L of 6M sodium hydroxide over 3 hours; seeded to obtain product as white solid, filtered it, washed it with 500 ml of water, and dried it at 50°/30 torr/8 hrs, and extracted it (37.62 g) from a large Soxhlet with a mixture of 350 ml of Freon® TF and 50 ml of dichloromethane. The extract was cooled to −20° to deposit 31.05 g (92%) of white 2-amino-4'-methoxydiphenyl sulfide, m.p. 64.5°–66°.

Anal. Calc. for $C_{13}H_{13}NO_3S$: C, 67.50; H, 5.67; N, 6.06%. Found: C, 67.32; H, 5.69; N, 6.00%.

The 2-amino-4'-methoxydiphenyl sulfide was subjected to diazotization, etc., according to the method on a related compound disclosed by P. Block, Jr., J. Am. Chem. Soc. 72, 5641–3 (1950), which is incorporated herein by reference, to give 7.5% of 2-methoxydibenzothiophene, m.p. 57.1°–58.4° (lit. m.p. 54°–55° for product prepared by a different method, M. Hori et al., Chem. Pharm Bull Japan 22, 1711–20 (1974)). After recrystallization from a mixture of methanol and t-butyl methyl ether at −20°. The PMR spectrum, 200 MHz, supported the structure.

The 2-methoxydibenzothiophene was subjected to a Friedel-Crafts acetylation as described for the corresponding dibenzofuran (as in Routier et al., supra) to give 55% of 3-acetyl-2-methoxy-dibenzothiophene, m.p. 163.4°–164.9° after recrystallization from a mixture of heptane and toluene. The PMR spectrum, 200 MHz, supported the structure.

Anal. Calc. for $C_{15}H_{12}O_2S$: C, 70.29; H, 4.72%. Found: C, 70.24; H, 4.79%.

In a 150 ml beaker 1.1 g of 3-acetyl-2-methoxydibenzothiophene in 25 ml of dioxane was stirred and heated to 55°. A mixture of 12 ml of 10.5% sodium hypochlorite, 12 ml of water, and 4.6 ml of 1M potassium hydroxide was added 1 ml at a time over 45 min, while heating to 57°. A heavy precipitate formed. About 1.2 g of sodium bisulfite was added to obtain a negative potassium iodide/starch paper test. Added 6M hydrochloric acid to obtain pH ≈2, cooled the mixture in ice to 5°, and filtered to obtain, after drying, 0.60 g (54%) of white 2-methoxydibenzothiophene-3-carboxylic acid, m.p. 249°–254°.

To prepare the non-ESIPT fluor 2-methoxy-3-(6'-methyl-2-benzoxazolyl)dibenzothiophene, a mixture of 2-methoxy-dibenzothiophene-3-carboxylic acid (0.97 g), 2-amino-5-methylphenol (0.463 g), 12 ml of bis(2-butoxyethyl) ether, and 0.10 g of boric acid was treated as in Example 2. The methylcyclohexane extract was cooled to −20° to obtain yellow powder, <0.04 g (3%) m.p. 218°–252°, a partially demethylated mixture.

To prepare the ESIPT fluor 2-hydroxy-3-(6'-methyl-2-benzoxazolyl)dibenzothiophene, the above mixture was boiled for 1 hr with 5 ml of sym-collidine and 0.042 g of lithium iodide, cooled, and filtered to give a solid, m.p. 276°–278°, which was recrystallized from 5 ml of 2-ethoxy-ethanol, yielding 0.031 g (90%) of orange powder, m.p. 276.5°–277.5°; fluorescence excitation maxima 337, 352 an 393 nm; emission 565 nm; $\Phi_f$=0.36 in toluene.

Anal. Calc. for $C_{20}H_{13}NO_2S$: C, 72.49; H, 3.95; N, 4.23%. Found: C, 72.16; H, 3.89; N, 4.14%.

Although the fluor in Example 4, differs from the fluor in Example 3 only in having a sulfur atom in place of the dibenzofuran 9-oxygen atom, a good $\Phi_f$ is maintained with a bathochromic shift of 20 nm in fluorescence. This bathochromic shift of the more electron-releasing sulfur atom demonstrates, by inference, that substitution of the sulfur atom by a nitrogen atom (making a carbazole, or N-alkylated carbazole) should also give a red-shift, but with higher $\Phi_f$, since nitrogen is less prone to quench fluorescence by spin-orbit coupling than is sulfur. The N-alkyl group in such a carbazole could be used to confer solubility in hydrocarbons or other non-polar solvents, thus allowing the use of an inexpensive 2-aminophenol as an intermediate.

EXAMPLE 5

Preparation of the fluor 2-hydroxy-3-(5-phenyl-2-benzoxazolyl)dibenzofuran was carried out as follows.

Into a 250 ml, 2-necked, round-bottomed flask, equipped with magnetic stirring, nitrogen inlet, and reflux condenser, were placed 8.88 g (36.7 mmole) of 3-carboxy-2-methoxy-dibenzofuran, 50 ml of dry tetrahydrofuran, 2.81 ml (38.5 mmole) of thionyl chloride, and 0.1 to 0.2 ml of N-methylpyrrolidinone. The mixture was refluxed for 2.5 hours and then allowed to cool to room temperature. Meanwhile, into a 3-necked, 500 ml, round-bottomed flask, equipped with magnetic stirring, a pressure-equalizing addition funnel, nitrogen inlet, and thermometer, were placed 7.13 g (38.5 mmole) of 2-amino-4-phenylphenol, 50 ml dry tetrahydrofuran, and 6.23 ml (77 mole) of pyridine. To this solution was added the cooled acid chloride solution over several minutes, resulting in an exotherm to 40° and the formation of a precipitate. The mixture was stirred for an additional hour, quenched by pouring it into 400 ml of water, and made acidic (pH ≈1). The solid was collected by vacuum filtration, washed with water, slurried in 500 ml of methanol, refiltered, and washed with an additional 200 ml of methanol, resulting in a brown solid. The solid was again slurried in 200 ml of methanol, filtered, washed with 50 ml of methanol, and dried (90°/30 torr/2 days), to give 9.53 g (64%) of N-(4-hydroxy-3-biphenyl)-2-methoxydibenzofuran-3-carboxamide, mp 227.5°–230.5°, dark melt or decomposition.

Into a 100 ml, 2-necked, round-bottomed flask, equipped with magnetic stirring, nitrogen inlet, a thermometer dipping into the solution, and a distillation head, were placed 9.00 g (22.0 mmole) of the amide, 0.23 g (3.7 mmole) of boric acid and 36 ml of diethyleneglycol dibutyl ether. The mixture was heated slowly (45 minutes) to reflux (255°–260°), held at this temperature for ½ hour, and then ≈⅔ (20–24 ml) of the solvent was removed by distillation. The remaining solution was cooled to ≈80° and poured into 100 ml of heptane, resulting in the formation of a semisolid. The mixture was boiled to break-up the solid and then cooled to −20°. The dark brown solid which resulted was filtered, washed with 25 ml heptane and dried (1 hour/90°) to give 8.36 g (97%) of solid. The solid was placed in a medium Ace-Kauffman column over 4 cm alumina and extracted with heptane. Once most of the fluorescent material had been eluted, the pot was cooled to −20°, the solid was filtered and dried (1.5 hours/70°) to give 5.48 g (64%) of 2-methoxy-3-(5-phenyl-2-benzoxazolyl)dibenzofuran, mp 155°–160°, res.

Into a 100 ml, 2-necked, round-bottomed flask, equipped with magnetic stirring, nitrogen inlet, and a condenser, were placed 5.2 g (13. mmole) of the methoxydibenzofuran, 3.12 g (23.4 mmole) of anhydrous lithium iodide, and 20 ml of collidine. The mixture was refluxed for one hour during which time the mixture thickened. The mixture was cooled somewhat and was poured into 150 ml of 3M hydrochloric acid. An additional 100 ml of water was added and the mixture was stirred at room temperature for ½ hour. The resulting solid was collected by filtration, washed with water and dried (16 hours/80°) to give 5.05 g of solid. The solid was placed in a medium Ace-Kauffman column over 4 cm alumina and extracted with ethyl acetate. Once all fluorescent material had been eluted, the pot was cooled to room temperature, the solid collected by filtration, washed with 30 ml ethyl acetate and dried (70°/5 hours) to give 4.69 g (94%) of pale yellow 2-hydroxy-3-(5-phenyl-2-benzoxazolyl)dibenzofuran, mp 293°–295°, shrinks 291°.

UV-Visible spectrum (toluene): 380 nm ($\epsilon$=35,100), 360 nm ($\epsilon$=32,600), 337 ($\epsilon$=46,300), 323 nm ($\epsilon$=32,200); Fl. Em. (toluene): 544 nm ($\Phi$=0.41).

Anal. Calc. for $C_{25}H_{15}NO_3$: C, 79.56; H, 4.01; N, 3.71. Found: C, 79.57; H, 4.06; N, 3.66.

EXAMPLE 6

Preparation of the fluor 3-(5-chloro-2-benzoxazolyl)-2-hydroxydibenzofuran was carried out as follows.

Into a 250 ml, 2-necked, round-bottomed flask, equipped with magnetic stirring, nitrogen inlet, and reflux condenser, were placed 10.00 g (41.3 mmole) of 3-carboxy-2-methoxy-dibenzofuran, 50 ml of dry tetrahydrofuran, 3.17 ml (43.4 mmole) of thionyl chloride, and 0.1 to 0.2 ml of N-methylpyrrolidinone. The mixture was refluxed for 2.5 hours and then allowed to cool to room temperature. Meanwhile, into a 3-necked, 500 ml, round bottomed flask, equipped with magnetic stirring, pressure-equalizing addition funnel, nitrogen inlet, and thermometer; were placed 6.23 g (43.4 mmole) of 2-amino-4-chlorophenol, 50 ml dry tetrahydrofuran, and 7.01 ml (87 mole) of pyridine. To this solution was added the cooled acid chloride over several minutes, resulting in an exotherm to 40° and the formation of a precipitate. The mixture was stirred overnight, quenched by pouring it into 400 ml of water, and made acidic (pH ≈1). The solid was collected by vacuum filtration, washed with water, slurried in 200 ml of methanol, refiltered, washed with an additional 50 ml of methanol, and dried (16 hrs/100°), resulting in 9.9 g (65%) of N-(2-hydroxy-5-chlorophenyl)-2-methoxy-dibenzofuran-3-carboxamide, mp 257°–259°.

Into a 100 ml, 2-necked, round-bottom flask, equipped with magnetic stirring, nitrogen inlet, thermometer dipping into the solution, and a distillation head; were placed 9.00 g (24.5 mmole) of the amide, 0.25 g (4.0 mmole) of boric acid and 36 ml of diethyleneglycol dibutyl ether. The mixture was heated slowly (45 minutes) to reflux (255°–260°), held at this temperature for ½ hour, and then ≈⅔ (25 ml) of the solvent was removed by distillation. The remaining solution was cooled to ≈80° and poured into 100 ml of heptane, resulting in the formation of a solid. The mixture was boiled to break up the solid and then cooled to −20°. The tan solid which resulted was filtered, washed with 25 ml heptane and dried (1 hour/90°) to give 8.77 g of solid, which was placed in a medium Ace-Kauffman column over 4 cm alumina and extracted with heptane. Once most of the fluorescent material had been eluted, the pot was cooled to −20°, the solid filtered and dried (1.5 hours/70°) to give 5.52 g (64%) of pale yellow 2-methoxy-3-(5-chloro-2-benzoxazolyl)dibenzofuran, mp 191°–193°.

Into a 100 ml, 2-necked, round-bottomed flask, equipped with magnetic stirring, nitrogen inlet, and a condenser, were placed 5.2 g (14.9 mmole) of the methoxydibenzofuran, 3.48 g (26.0 mmole) of anhydrous lithium iodide and 20 ml of collidine. The mixture thickened during reflux, necessitating the addition of an additional 40 ml of collidine to aid with stirring. The mixture was boiled under reflux, cooled somewhat and was poured into 200 ml of 3M hydrochloric acid. An additional 200 ml of water was added and the mixture was stirred at room temperature for ½ hour. The resulting solid was collected by filtration, washed with water and dried (16 hours/80°) to give 5.16 g of solid. The solid was placed in a medium Ace-Kauffman column over 4 cm alumina and extracted with heptane. Once all fluorescent material had been eluted the pot was cooled to room temperature, the solid collected by filtration, and dried (70°/5 hours) to give 3.56 g (71%) of pale yellow 3-(5-chloro-2-benzoxazolyl)-2-hydroxydibenzofuran, mp 244°–246°.

UV-VIS (toluene): 379 nm ($\epsilon$=34,400), 360 nm ($\epsilon$=32,900), 337 ($\epsilon$=49,000), 323 nm ($\epsilon$=36,500); Fl. Em. (toluene): 545 nm ($\Phi$=0.32).

Anal. Calc. for $C_{19}H_{10}NO_3Cl$: C, 67.97; H, 3.00; N, 4.17. Found: C, 68.21; H, 3.05; N, 4.12.

EXAMPLE 7

The fluor 3-(9,9-dipropylindeno[3,2-f]benzoxazol-3-yl-2-hydroxydibenzofuran was prepared as follows.

A 1 liter, 3-necked, round bottomed flask, equipped with condenser, nitrogen inlet, thermometer, mechanical stirring, and pressure equalizing addition funnel and containing 10.80 g (0.444 mole) of magnesium was purged with nitrogen and heated to 110° for 1 hour. Meanwhile, 133.0 g (0.404 mole) of 2-bromo-9,9-dipropylfluorene was dissolved in 300 ml dry tetrahydrofuran, along with ≈0.5 ml 1,2-dibromoethane, and ≈100 ml of the solution was added to the hot magnesium. The mixture was heated to reflux, and after a short period, formation of the Grignard reagent ensued, resulting in spontaneous boiling. The remainder of the bromide was added at a rate sufficient to maintain reflux. The solution was boiled under reflux for an additional 1 hour after addition was complete and then cooled to room temperature.

Into a 2-liter round-bottomed flask, equipped with mechanical stirring, pressure equalizing addition funnel, thermometer, and nitrogen inlet, were placed 50.5 ml of trimethyl borate and 250 ml of dry tetrahydrofuran. The solution was cooled to −10° in an acetone/ice bath and the Grignard solution was added (transferred via needle) at −10° to −5° with vigorous stirring. The solution was stirred an additional 15 minutes and 34.5 ml of cold glacial acetic acid was added all at once, followed by the addition of a cold solution of 30% hydrogen peroxide in 40 ml water dropwise, keeping the temperature below 0°. The mixture was allowed to warm over a 30 minute period and was washed repeatedly with portions of a saturated solution of ammonium sulfate (1 liter total). The organic layer was washed over magnesium sulfate and concentrated to give a dark oil. The oil was distilled under vacuum. The distillate was recrystallized from heptane (3–4 ml/g) at −20° to give 30.5 g (28%) of colorless 9,9-dipropyl-2-hydroxyfluorene, mp 116°–117°.

Into a 1-liter, 3-necked, round-bottomed flask, equipped with magnetic stirring, thermometer, and pressure equalizing addition funnel, were added 200 ml of glacial acetic acid and 8.00 g (30.0 mmole) of 2-hydroxy-9,9-dipropylfluorene. Concentrated (70%) nitric acid was then added dropwise over a 15 minute period, keeping the temperature below 30° with the aid of a water bath. The mixture was heated for 1 hour at 80°–90°, cooled and poured into 500 ml water, resulting in the formation of an emulsion. The mixture was extracted with three 200 ml portions of methylene chloride and the combined organic layers were dried over magnesium sulfate and concentrated. The resulting oil was dissolved in cyclohexane/toluene (8:2) and passed through 10 cm×2.5 cm of Silica Gel with cyclohexane/toluene (8:2) as the eluent. The eluate was concentrated; the resulting oil dissolved in ethanol (50 ml), and the solution poured into water (250 ml) to precipitate the product as a yellow solid. The solid was collected by filtration, washed with water and dried (2.5 hours/mechanical pump) to give 7.09 g (72%) of yellow 9,9-dipropyl-2-hydroxy-3-nitrofluorene, mp 98°–101°.

Into a 1 liter, 3-necked, round-bottomed flask, equipped with magnetic stirring, thermometer, nitrogen inlet and pressure equalizing addition funnel, were added 2.8 g of wet 10% palladium/carbon catalyst, 100 ml of ethanol/water (1:1), and 8.42 (0.223 mole) of sodium borohydride dissolved in 150 ml of ethanol/water (1:1). To this solution, 34.8 g (0,106 mole) of the nitrophenol dissolved in a solution of 150 ml of water, 200 ml methanol, and 200 ml ethanol, containing as well 40 g (1.06 mole) of sodium hydroxide, was added dropwise over 1 hour. The mildly exothermic reaction was kept under 30° with the aid of a cold water bath. The reaction mixture was stirred for an additional hour after addition was complete and then filtered through polyester cloth to remove the catalyst. The filtrate was quenched by pouring it into 2 liters of water and the diluted mixture was neutralized with 6M hydrochloric acid (pH 6.5–7.0), resulting in the formation of a pink precipitate, which was collected by vacuum filtration and washed with a copious amount of water. After drying (overnight/mechanical pump), 30.5 g of 3-amino-9,9-dipropyl-2-hydroxyfluorene, mp 174°–178° dec. was obtained.

Into a 250 ml, 2-necked, round-bottomed flask, equipped with magnetic stirring, nitrogen inlet, and reflux condenser, were placed 6.98 g (28.8 mmole) of 3-carboxy-2-methoxydibenzofuran, 50 ml of dry tetrahydrofuran, 2.20 ml (30.2 mmole) of thionyl chloride, and 0.1 to 0.2 ml of N-methylpyrrolidinone. The mixture was refluxed for 2.5 hours and then allowed to cool to room temperature. Meanwhile, into a 3-necked, 500 ml, round bottomed flask, equipped with magnetic stirring, pressure-equalizing addition funnel, nitrogen inlet, and thermometer, were placed 8.99 g (30.2 mmole) of 3-amino-9,9-dipropyl-2-hydroxyfluorene, 50 ml dry tetrahydrofuran, and 4.77 ml (60.4 mole) of pyridine. To this solution was added the cooled acid chloride over several minutes, resulting in an exotherm and the formation of a precipitate. The mixture was stirred for an additional 1 hour, quenched by pouring into 400 ml of water, and made acidic (pH ≈1). The solid was collected by vacuum filtration, washed with water, slurried in 200 ml of methanol, refiltered, and washed with an additional 100 ml of methanol, resulting in a yellow solid. After drying obtained 10.5 g (70%) of N-(9,9-dipropyl-2-hydroxy-3-fluorenyl)-2-methoxydibenzofuran-3-carboxamide, mp 252°–255°.

Into a 100 ml, 2-necked, round-bottomed flask, equipped with magnetic stirring, nitrogen inlet, thermometer dipping into the solution, and a distillation head, were placed 10.00 g (19.2 mmole) of the amide, 0.20 g (3.2 mmole) of boric acid and 40 ml of diethyleneglycol dibutyl ether. The mixture was heated slowly (45 minutes) to reflux (255°–260°), held at this temperature for ½ hour, and then ≈¾ (30 ml) of the solvent was removed by distillation. The remaining solution was cooled to ≈80° and poured into 200 ml of heptane, resulting in the formation of a solid. The mixture was stirred to break up the solid and then cooled to −20°. The solid was filtered, washed with 25 ml of heptane and dried (1 hour/90°). The filtrate was concentrated and dried (100°/mechanical pump) to yield an additional 2 g of solid. The combined solids were placed in a medium Ace-Kauffman column over 4 cm alumina and extracted with heptane. Once most of the fluorescent material had been eluted, the pot was cooled to −20°, the solid filtered and dried (16 hours/80°) to give 7.25 g (75%) of a salmon solid, 3-(9,9-dipropylindeno[3,2-f]benzoxazol-3-yl-2-methoxydibenzofuran, mp 158°–165°, cloudy melt.

Into a 100 ml, 2-necked, round-bottomed flask, equipped with mechanical stirring, nitrogen inlet, and a condenser, were placed 6.75 g (13.4 mmole) of the methoxydibenzofuran, 3.16 g (23.6 mmole) of anhydrous lithium iodide, and 25 ml of collidine. The mixture was refluxed for 1.5 hours during which time the mixture thickened and then all solids dissolved. The mixture was cooled somewhat and was poured into 250 ml of water and made acidic (pH 1–2) with concentrated hydrochloric acid. An additional 200 ml of water was added and the mixture was stirred at room temperature for ½ hour. The resulting solid was collected by filtration, washed with water and dried (16 hours/80°). The solid was placed in a medium Ace-Kauffman column over 4 cm alumina and extracted with ethyl acetate. Once all fluorescent material had been eluted, the pot was cooled to room temperature, the solid collected by filtration, washed with 30 ml ethyl acetate and dried (70°/5 hours) to give 5.77 g (88%) of pale yellow 3-(9,9-dipropylindeno[3,2-f]benzoxazol-3-yl-2-hydroxydibenzofuran, mp 304°–305°, shrinks 303°.

UV-VIS (toluene): 389 nm ($\epsilon$=54,300), 369 nm ($\epsilon$=48,900), 345 ($\epsilon$=42,200), 329 nm ($\epsilon$=24,100), 315 nm ($\epsilon$=21,600); Fl. Em. 543 nm ($\Phi$=0.44).

Anal. Calc. for $C_{32}H_{27}NO_3$: C, 81.16; H, 5.75; N, 2.96. Found: C, 80.69; H, 5.66; N, 2.90.

Figure 4:
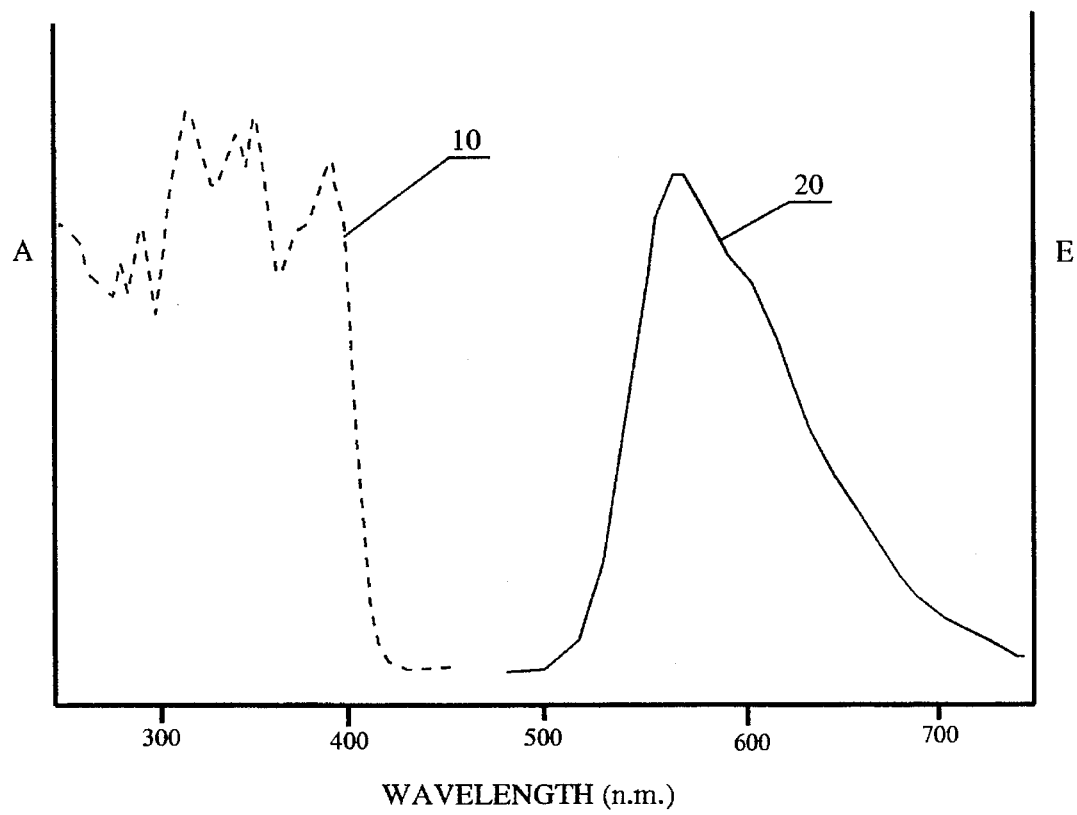
FIG. 4 illustrates the Stokes shift of the emission spectrum for a 2-benzazolyl compound of this invention.

The fluors of Examples 1–7 are unusual, as UV absorbers, because they display an unusually sharp cutoff, as shown in FIG. 4 for the fluor of Example 4, which is typical. In FIG. 4, the long-wave end of the excitation bands, which is similar in appearance to the UV absorption bands (10), drops off very steeply, i.e., relative to maximum peak absorption, from 90% at 400 nm, down to 10% at 411 nm. Such a cutoff traverses only 11 nm, minimizing color distortion of the visible light transmitted. In comparison, a more typical organic molecule, such as trans-azoxybenzene, has 90–10% falloff in absorption fully 40 nm wide, from 90% of the peak long-wave absorption at 350 nm to 10% of the peak at 390 nm (H. H. Jaffe and Milton Orchin, "Theory and Applications of Ultraviolet Spectroscopy", John Wiley & Sons, New York, 1962, p. 431). FIG. 4, likewise, illustrates the substantial Stokes shift of about 100 nm or more for the ESIPT fluorescence emission (20) of the fluor of Example 4 which peaks at 565 nm and which is typical of the 2-benzazolyl compounds of this invention.

EXAMPLE 8

Styrene was de-inhibited by passage through alumina and distilled under vacuum. Silanized polymerization tubes were doped with 1.25% p-terphenyl, a primary fluor, and 0.01% of 3-hydroxyflavone (3HF, a recognized standard secondary fluor for comparison) or 0.01% of the fluor of Example 1, then the styrene was added. The solutions were degassed through repeated freeze-thaw-pump cycles and heated at 125° for 24 hrs and 140° for 48 hrs, cooled slowly to 90°, and placed in liquid nitrogen for release of the doped polystyrene. Cylinders 2.2 cm in diameter and 1 cm high were machined and polished.

The polymer containing either the fluor of Example 1 or 3HF were similar in degree of radiation damage and recovery therefrom on exposure to 10 Mrad from cobalt-60 gamma rays. They were also similar in scintillation decay time, which was 8.6±0.2 nsec. The polymer containing the fluor of Example 1 was 10% brighter than the polymer containing 3HF on excitation with 334 nm photons. The emission maximum of the polymer containing the fluor of Example 1 was 540 nm, while emission maximum of the polymer containing 3HF was 530 nm (A. Pla-Dalmau and A. D. Bross, Proc. Intl. Mtg. Materials Res. Soc., San Francisco, Calif., 4–8 Apr 94).

The fluors of Examples 1–7 above are unusually chemically, thermally (to ≧300° C.), and photochemically stable; much more so than 3HF, which decomposes in the presence of oxygen, for which a mechanism has been reported by S. L. Studer and W. E. Brewer, M. L. Martinez, P.-T. Chou, in J. Am. Chem. Soc. 111, 7643 [1989]. The decomposition products of 3HF and other flavones absorb light in much of the visible range, appearing orange or brown to the eye, and reducing the light output of a scintillator such as that of Example 8, and particularly, for a scintillating optical fiber.

EXAMPLE 9

The fluor of Example 3, Oxazole 545M6', was incorporated into optical grade polycarbonate resin at 0.1 gram per pound of polymer, along with a typical additive package, to form, after injection molding, a lens-like plate 50 mm in diameter and 2 mm thick. The plate appeared colorless to the eye, and is considered to have a UV cutoff of about 388 nm. The transmittance properties are given in Table 1:

TABLE 1

| wavelength | % Transmittance |
| --- | --- |
| 200–380 nm | 0.0 |
| 390 | 3.0 |
| 400 | 63.3 |
| 410 | 83.8 |
| 420 | 86.6 |
| 430–770 | 87.3–90.4 |

Such plate or sheet material are particularly useful in the manufacture of protective eye-ware such as optical lenses for eyeglasses, sunglasses, or saftey glases; or optically clear face shields. Such protective eye-ware comprises a plastic sheet material which is optically clear and transparent in a portion of the visible spectral region and is substantially opaque to UV radiation, wherein the plastic sheet material comprises: a polymeric matrix material, and a 2-benzazolyl compound having the structure of Formula I, supra. The lenses or face shield of the protective eye-ware typically appears colorless to the eye, but in the case of sunglasses, and the like, may contain a colorant to provide a suitable tint. Polycarbonate is a prefered polymeric matrix material although other acrylic, styryl, or vinyl polymeric materials described supra may also be used.

EXAMPLE 10

The fluor 9-ethyl-3-hydroxy-2-(6'-methyl-2-benzoxazolyl) carbazole, was prepared according to the synthesis illustrated in FIG. 3 as follows.

A solution of 5'-methoxy-2'-nitroacetanilide (21.0 g, 0.100 mole, R. M. Acheson et al., J. Chem. Soc., 1117 [1978]) and sodium acetate (8.37 g, 0.102 mole) in 125 ml of acetic acid was heated with stirring to 55°. Then bromine (16.16 g, 5.2 ml, 0.101 mole) was added during about 15 min. at 55°, followed by 30 min. at this temperature. The nearly colorless mixture was quenched in 400 ml of water containing 1 g of sodium bisulfite. Yellow needles of 4'-bromo-5'-methoxy-2'-nitroacetanilide were collected on a filter, washed with 500 ml of water, and dried, to obtain 25.8 g, m.p. 127.5°–133.5°. This was recrystallized from 250 ml of toluene to give 18.0 g (62%), m.p. 139°–140.5°.

Anal. Calc. for $C_9H_8BrN_2O_4$: C, 37.52; H, 2.80; N, 9.72; Br, 27.74. Found: C, 37.77; H, 2.91; N, 9.80; Br, 27.69.

IR Spectrum in $cm^{-1}$ (Perkin-Elmer 283, 2.6% w/v chloroform): 3320, (N—H); 3015, (Ar—H); 1702, (C=O); 1592, (NH); 1582, (C=C); 1488, ($NO_2$); 1330 ($NO_2$); 1205, (Ar—O); 1053, ($CH_3O$); 862 (C—$NO_2$).

PMR Spectrum (Varian EM360L, 8% in $CDCl_3$): δ2.29 (s, 3H, —C(=O)$CH_3$); 4.00 (s, 3H, —$COCH_3$); 8.41 (s, 1H, H6); 8.65 (s, 1H, H̄3); 10.71 ppm (br s, 1H̄, N̲H̲).

Hydrolysis of this amide was accomplished by refluxing it (17.6 g, 0.069 mole) with a mixture of 75 ml of 12M hydrochloric acid and 15 ml of acetic acid for 1 hour, during which time 4-bromo-5-methoxy-2-nitroanilinium chloride separated as flakes. After addition of 125 ml of water, the solid was filtered and dried to give the free base as tiny yellow needles, m.p. 175.5°–178.5°, 14.0 g (93%).

Anal. Calc. for $C_7H_7BrN_2O_3$: C, 34.03; H, 2.86; N, 11.34; Br, 32.34. Found: C, 34.14; H, 2.84; N, 11.38; Br, 33.19.

IR Spectrum in $cm^{-1}$ (Perkin-Elmer 283, 2% w/v chloroform): 3512, ($NH_2$); 3388, ($NH_2$); 3015, (Ar—H); 2975, ($CH_3$); 2940, ($CH_3$); 2840, ($CH_3$); 1618, ($NH_2$); 1585, (C=C); 1490, ($NO_2$); 1363 ($NO_2$); 1208, (Ar—O); 1042, ($CH_3O$).

PMR Spectrum (Varian EM360L, 4.5% in Unisol-d): δ3.95 (s, 3H, —$COCH_3$); 6.53 (s, 1H, H6); 8.24 (s, 1H, H3); 6.99 (br s, 2H, N̲H̲$_2$).

A mixture of the 4-bromo-5-methoxy-2-nitroaniline (98.6 g, 0.400 mole), 70 ml of water, 120 ml of 12M hydrochloric acid, and 1000 ml of benzene was stirred well and treated with a solution of sodium nitrite (27.6 g, 0.400 mole) in 50 ml of water at 18°–10° during about 1 hour. Since some tan solid remained, more sodium nitrite was added so that nearly all solid dissolved. Rapid stirring at 26° for 20 hours was followed by a similar period at 40°. The mixture was cooled in ice to 10°, filtered from a little solid, the filtrate separated, and the organic layer was washed with 800 ml, then 300 ml of 10% sodium chloride, dried over potassium carbonate, and evaporated to obtain 108 g of dark oil which was distilled through a heated Claisen until decomposition in the pot began. An orange oil was obtained, b.p. 198°/1.3 torr–165°/0.8 torr, 75 g (61% crude) of 4-bromo-2-nitro-5-methoxybiphenyl, which was used without further purification.

For assays, some material that crystallized on keeping and scratching was recrystallized from ethanol to give tan spars, m.p. 90°–91°.

Anal. Calc. for $C_{13}H_{10}BrNO_3$: C, 50.67; H, 3.27; N, 4.55; Br, 25.93. Found: C, 50.99; H, 3.38; N, 4.53; Br, 25.89.

IR Spectrum in $cm^{-1}$ (Perkin-Elmer 283, 5.5% w/v chloroform): 3010, (Ar—H); 2975, ($CH_3$); 2943, ($CH_3$); 2853, ($CH_3$); 1593, (C=C); 1563, (C=C); 1518, (C=C); 1480, ($NO_2$); 1342 ($NO_2$); 1210, (Ar—O); 1036, ($CH_3O$); 698, (ArH).

The biphenyl (75 g, 0.243 mole) was boiled under reflux with 200 ml of triethyl phosphite for 19 hours under argon. Excess triethyl phosphite and by-product triethyl phosphate were removed by distillation at 0.8 torr. The residue was taken up in 200 ml of 1-propanol later diluted with 50 ml of water, and cooled to 5°. The 2-bromo-3-methoxy carbazole crystallized, was filtered and washed with methanol to give, after drying, 14.8 g of tan solid, m.p. 187°–192°. This was extracted from 3 cm of alumina (Aldrich 19,997-4) in a medium Ace-Kauffman column with a mixture of 300 ml of heptane and 30 ml of toluene. The extract was cooled in ice, filtered, washed with hexane, and dried to give 13.6 g (20%) of white solid, m.p. 193°–195°.

Anal. Calc. for $C_{13}H_{10}BrNO$: C, 56.55; H, 3.65; N, 5.07; Br, 28.94. Found: C, 56.75; H, 3.77; N, 5.11; Br, 29.17.

IR Spectrum in $cm^{-1}$ (Perkin-Elmer 283, 1% w/v chloroform): 3470, (NH); 3010, (ArH); 2960, ($CH_3$); 2940, ($CH_3$); 2840, ($CH_3$); 1605, (CN); 1592, (C=C); 1462, (v.s., C=C); 1449, (C=C); 1200, (Ar—O); 1045, ($CH_3O$).

The carbazole (13.32 g, 0.0482 mole) was added in portions to sodium hydride (2.02 g of 60% in oil, 0.0506 mole, previously washed with ether) under 70 ml of dry N,N-dimethylformamide below 17° in an ice bath. When evolution of hydrogen ceased, ethyl iodide (4.2 ml, 0,053 mole) was added dropwise at 9°–11°. An exotherm to 24° was followed by deliberate heating to 50°. The solvent was evaporated, and the residue was partitioned between 100 ml of t-butyl methyl ether and 50 ml of water. The organic layer was filtered through Whatman 1 PS paper and evaporated to yield 13.7 g (93% crude) of pale oily 2-bromo-3-methoxy-9-ethylcarbazole, which was used without further purification.

The analytical sample was obtained by recrystallization from 2-propanol/acetone, then ethanol; m.p. 85.5°–87.5° as white needles.

Anal. Calc. for $C_{15}H_{14}BrNO$: C, 59.23; H, 4.64; N, 4.60; Br, 26.27. Found: C, 59.37; H, 4.77; N, 4.63; Br, 26.62.

IR Spectrum in $cm^{-1}$ (Perkin-Elmer 283, 5% w/v chloroform): 3008, (ArH); 2986, ($C_2H_5$); 2938, ($CH_3$); 2895, ($C_2H_5$); 2840, ($CH_3$); 1599, (CN); 1486, (C=C); 1470, (v.s., C=C); 1441, (C=C); 1200, (Ar—O); 1036, ($CH_3O$).

The 9-ethylcarbazole (13.0 g, 0.0428 mole) and copper(I) cyanide (4.60 g, 0.0513 mole) in 15 ml of N,N-dimethylformamide were boiled under reflux for 19 hours with powerful magnetic stirring. All dissolved within 40 min. When cooled to ≈60° the mixture was treated with a solution of 10.5 g of potassium cyanide in 35 ml of water, and stirred 1 hour. The solid was filtered, the lumps being broken up, washed on the Büchner with 250 ml of water, and dried to give 11.0 g of crude 2-cyano-9-ethyl-3-methoxy carbazole, m.p. 145°–155°. This was extracted from a Soxhlet overnight with 250 ml of heptane and the extract was cooled in ice to give 9.70 g (91%), m.p. 148°–155.5°. TLC on MK6F Silca Gel, t-butyl methyl ether, UV showed 5–10% of a non-fluorescent impurity at Rf=0.65 and 90–95% ArCN with a blue fluorescence at Rf=0.69. This was used in the next reaction.

The analytical sample was prepared by means of two recrystallizations from 1-propanol to give huge prisms, m.p. 158°–160°.

Anal: Calc. for $C_{16}H_{14}N_2O$: C, 76.78; H, 5.64; N, 11.19. Found: C, 76.86; H, 5.60; N, 11.26.

IR Spectrum in cm$^{-1}$ (Perkin-Elmer 283, 4% w/v chloroform): 3010, (ArH); 2980, ($C_2H_5$); 2940, ($CH_3$); 2890, ($C_2H_5$); 2840, ($CH_3$); 2224, (C≡N); 1630, (C—N); 1492, (C=C); 1475, (v.s., C=C); 1464, (C=C); 1434, (C=C); 1202, (Ar—O); 1028, ($CH_3O$).

In a 500 ml flask on a mantle with magnetic stirring, was placed 120 ml of water and 85% potassium hydroxide pellets (9.89 g, 0.150 mole), and stirred to obtain a solution. Then the above nitrile (9.40 g, 0.0375 mole) and 150 ml of glycol were added. Solvent was distilled to obtain a reaction temperature of 135°, and the mixture was boiled under reflux for 24 hours, and cooled to 25°. The almost clear solution was filtered, and the filtrate was acidified with 30 ml of 6M hydrochloric acid. The resulting gum was stirred mechanically for 40 min., filtered, washed with water, then 50% methanol, and dried to give 9.29 g of 3-methoxy-9-ethylcarbazole-2-carboxylic acid, m.p. 158°–160.5°. This was recrystallized from 70 ml of xylenes at 0° to give 7.74 g (76%), m.p. 158.5°–160.5°; mixed with the nitrile, m.p. 130°–147°. A second crop of 0.78 g (8%) of lower quality was obtained on cooling filtrates to −20°.

The analytical sample was prepared by recrystallization from 20 ml/g of 1-butanol, m.p. 162°–163°.

Anal: Calc. for $C_{16}H_{15}NO_3$: C, 71.36; H, 5.61; N, 5.20. Found: C, 71.35; H, 5.65; N, 5.21.

IR Spectrum in cm$^{-1}$ (Perkin-Elmer 283, 4% w/v chloroform): 3260, (br, OH); 3010, (ArH); 2980, ($C_2H_5$); 2945, ($CH_3$); 2848, ($CH_3$); 1722, (v.s., C=O); 1631, (C—N); 1474, (v.s., C=C); 1439, (C=C); 1205, (Ar—O); 1022, ($CH_3O$).

A mixture of the above acid (1.87 g, 0.00695 mole), 6-amino-m-cresol (0.856 g, 0.00695 mole, Lancaster 6565), 0.08 g of boric acid, and 12 ml of bis(2-butoxyethyl) ether was heated with stirring under argon under a T-head so that the water formed, distilled out, then under reflux at 256° for 1 hour. A total of 7 ml of solvent distilled. When cooled to 25°, the mixture was quenched in 20 ml of methanol, cooled to −20° when some crystals appeared, then to −65°; filtered and dried to give 0.25 g of yellow solid, m.p. 178°–190°, a mixture of 9-ethyl-3-methoxy-2-(6-methyl-2-benzoxazolyl)carbazole (i.e., ArOMe) and the 3-hydroxy analog (i.e., ArOH). The filtrates were diluted to 50 ml with methanol and kept at −20° overnight for a second crop of 0.17 g; total 0.42 g (17% crude). This mixture was used in the next step.

The above mixture of ArOMe and ArOH (0.42 g, ≈0.0012 mole) and lithium iodide (0.30 g, 0.0022 mole) in 5 ml of 2,4,6-collidine was boiled under reflux, with stirring and argon, for 1 hour; cooled to ≈40°, and quenched in 25 ml of 3M hydrochloric acid. This mixture was filtered and dried to give 0.41 g of crude 9-ethyl-3-hydroxy-2-(6-methyl-2-benzoxazolyl)carbazole, which was extracted from 3 cm of alumina (Aldrich 19,997-4) with 30 ml of ethyl acetate. The clear, dark orange extract was kept at −65° to give 0.262 g (66%) of pure product, m.p. 195°–197.5°. This material showed an intense orange fluorescence in the solid state or in toluene solution or in contact with water under long-wave ultraviolet excitation, with no visible daylight-excited fluorescence.

Anal: Calc. for $C_{22}H_{18}N_2O_2$: C, 77.17; H, 5.30; N, 8.18. Found: C, 76.54; H, 5.36; N, 7.91.

UV-VIS (toluene): 346 nm (ε=48,500), 362 nm (ε=41,400), 401 nm (ε=6,700), 420 nm (ε=8,200); Fl. Em. 597 nm (Φ=0.17).

EXAMPLE 11

The fluor 2-(9,9-dipropylindeno[3,2-f]-2-benzoxazolyl)-9-ethyl-3-hydroxy-carbazole, was prepared according to the synthesis illustrated in FIG. 3 as follows.

Condensation of 3-methoxy-9-ethylcarbazole-2-carboxylic acid with 3-amino-9,9-dipropyl-2-hydroxyfluorene was carried out as described above Example 10 to give, after dilution of the cooled mixture with methanol and storing it at −20°, a yellow solid in 25% crude yield, m.p. 245°–265°. TLC on MK6F Silica Gel, t-butyl methyl ether, showed ≈40% of ArOMe with a blue fluorescence under long-wave ultraviolet excitation at Rf=0.73, and ≈60% ArOH with a pink-orange fluorescence at Rf=0.80. This mixture was used in the next step.

The above mixture (0.48 g, 0.906 mole) and lithium iodide (0.24 g, 1.800 mole) was refluxed in 5 ml of 2,4,6-collidine with stirring under argon for 1 hour, cooled to ≈40° and quenched in 25 ml of 3M hydrochloric acid. The precipitated solid was washed with methanol and dried to give 0.44 g (94% crude), which was extracted as in Example 10 to give, on cooling to 25°, 0.060 g (13%) of huge yellow spars, m.p. 278.5°–280.5°; this product was used for assays and electronic spectra. A second crop at −20°, m.p. 276.5°–277.5°, 0.240 g (51%, total 64%) was obtained. This material showed an intense orange fluorescence (more intense than that of the product of Example 10) in the solid state or in toluene solution or in contact with water under long-wave ultraviolet excitation, with no visible daylight-excited fluorescence.

Anal: Calc. for $C_{34}H_{32}N_2O_2$: C, 81.57; H, 6.44; N, 5.60. Found: C, 80.95; H, 6.28; N, 5.66.

UV-VIS (toluene): 321 nm (ε=14,500), 360 nm (ε=57,200), 375 nm (ε=48,000), 423 nm (ε=11,100); Fl. Em. 600 nm (Φ=0.21).

The fluors of Examples 10 and 11 possess a fluorescence which is bathochromically shifted into the orange region. While other ESIPT fluors are known with emission peaks ranging from 571 to 650 nm, such as those reported by A. Sytnik and M. Kasha, Radiat. Phys. Chem. 41, 331 (1993), none of the known fluors have all the other desirable attributes of practical fluors, i.e., good chemical and photochemical stability, high extinction coefficient and high fluorescence quantum yield. In scintillation counting utilizing polystyrene fibers, the 575 nm region is the most transmissive in radiation damaged polystyrene. Very importantly, the type of light detector most favored in scintillation detection, is changing from a photomultiplier tube (PMT) to a charge-coupled device (CCD). Where the sensitivity of the PMT is greatest at ≈400 nm, sensitivity drops between 500 and 600 nm for even green-extended PMTs. The response of CCDs is just the opposite. CCDs are as much as 70% more sensitive at 600 nm than at 500 nm.

Bis-benzazolyl compounds of this invention may be prepared using the type of general reaction sequences as hereinabove set forth. Illustrative of such bis-benzazolyl compounds are the following bis-benzoxazolyl compounds but is not intended to be limited thereby: 3,6-bis-(2-benzoxazolyl)-2-hydroxydibenzofuran; 3,6-bis-(6-methyl-2-benzoxazolyl)-2-hydroxydibenzothiophene; 2,7-bis-(6'-methyl-2-benzoxazolyl)-9-ethyl-3-hydroxycarbazole; and the like. Such bis-benzazolyl compounds are expected to have exceedingly high extinction coefficients with concomitant short fluorescence lifetimes.

Benzimidazolyl and benzothiazolyl compounds of this invention may be prepared using the type of general reaction sequences as hereinabove set forth as further modified by conventional preprative proceedures for benzimidazolyl and benzothiazoyl moieties. Illustrative of such benzazolyl compounds are the following benzoxazolyl compounds but is not intended to be limited thereby: 2-hydroxy-3-(2-benzimidazolyl)-dibenzofuran; 2-hydroxy-3-(2-benzothiazolyl)dibenzofuran; 2-hydroxy-3-(6-methyl-2-benzimidazolyl)dibenzothiophene; 2-hydroxy-3-(6-methyl-2-benzothiazolyl)dibenzothiophene; 9-ethyl-3-hydroxy-2-(6'-methyl-2-benzimidazolyl)carbazole; 9-ethyl-3-hydroxy-2-(6'-methyl-2-benzothiazolyl)carbazole; and the like. Such fluors containing a benzimidazolyl or benzothiazolyl moiety are expected to possess absorption and fluoresence emission spectra with a substantial bathochromic shift when compared to that of similar benzoxazolyl compounds. In particular the 3-hydroxy-2-(2-benzothiazolyl)carbazole compounds are expected to fluoresce in the red spectral region and particularly would be suited for applications in scintillation detection using a charge-coupled device (CCD) as discussed supra.

Those skilled in the art having the benefit of the teachings of the present invention as hereinabove set forth, can effect numerous modifications thereto. These modifications are to be construed as being encompassed within the scope of the present invention as set forth in the appended claims.

What is claimed is:

1. An organic, fluorescent material comprising a 2-benzazolyl compound having the structure:

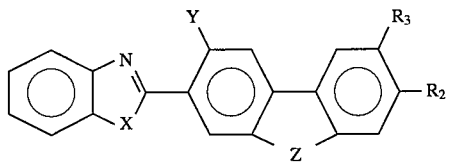

wherein X is a —N(R$_1$)— group, —O—, or —S—; Y is a proton donating group; Z is a —N(R$_1$)—group, —O—, or —S—; R$_1$ is a H or a C$_1$ to C$_{10}$ alkyl group; R$_2$ is a H or an added 2-benzazolyl group; R$_3$ is a H when R$_2$ is a H and R$_3$ is H or a Y when R$_2$ is an added 2-benzazolyl group; and the 2-benzazolyl, the added 2-benzazolyl, or both the 2-benzazolyl and the added 2-benzazolyl is unsubstituted or substituted with one to four R$_4$ group(s), wherein each R$_4$ individually is a C$_1$ to C$_{10}$ alkyl group, aryl group, halo group, or alkyl sulfonyl; or wherein two or more R$_4$ groups are fused into an aromatic group.

2. The organic, fluorescent material of claim 1 wherein the proton transfer group Y is a hydroxy group.

3. The organic, fluorescent material of claim 1 wherein the proton transfer group Y is an amido group, or a sulfonamido group of the structure: —NH—SO$_2$—R$_5$ wherein R$_5$ is a C$_1$ to C$_{10}$ alkyl group or aryl group.

4. The organic, fluorescent material of claim 3 wherein R$_5$ is a methyl, an ethyl, a propyl, a butyl, a phenyl or a tolyl group.

5. The organic, fluorescent material of claim 1 wherein the added 2-benzazolyl group is the same as the 2-benzazolyl.

6. The organic, fluorescent material of claim 1 wherein the 2-benzazolyl, the added 2-benzazolyl, or both the 2-benzazolyl and the added 2-benzazolyl is a 2-benzoxazolyl group.

7. The organic, fluorescent material of claim 1 wherein the 2-benzazolyl compound is taken from the group consisting of 3-(9,9-dipropylindeno[3,2-f]benzoxazol-2-yl)-2-hydroxydibenzofuran, 3-(5-chloro-2-benzoxazolyl)-2-hydroxydibenzofuran, 2-hydroxy-3-(5-phenyl-2-benzoxazolyl)dibenzofuran, 2-hydroxy-3-(6-methyl-2-benzoxazolyl)dibenzothiophene, 2-hydroxy-3-(6-methyl-2-benzoxazolyl)dibenzofuran, 2-hydroxy-3-(5-methyl-2-benzoxazolyl)dibenzofuran, 2-hydroxy-3-(2-benzoxazolyl)dibenzofuran, 9-ethyl-3-hydroxy-2-(6'-methyl-2-benzoxazolyl)carbazole, and 2-(9,9-dipropylindeno[3,2-f]-2-benzoxazolyl)-9-ethyl-3-hydroxycarbazole.

8. The organic fluorescent material of claim 1 wherein the 2-benzazolyl compound absorbs electromagnetic radiation in the spectral region about 420 nm or shorter and fluoresces in the visible spectral region about 520 nm or longer.

9. The organic fluorescent material of claim 8, wherein the 2-benzazolyl compound has an extinction coefficient of about 40,000 or greater in the spectral region of about 420 nm or shorter and has a fluorescence quantum yield of about 0.3 or greater in the visible spectral region of about 520 nm or longer.

10. The organic fluorescent material of claim 8 wherein the 2-benzazolyl compound is substantially transparent to its own fluorescence emission within the visible spectral region.

11. The organic fluorescent material of claim 1 wherein the 2-benzazolyl compound is dispersed in a matrix material which is transparent in at least a portion of the visible electromagnetic radiation spectrum.

12. The organic fluorescent material of claim 11 wherein the matrix material is a solid polymeric material.

13. The organic fluorescent material of claim 12 wherein the solid polymeric material is a vinyl, a styryl, or an acrylic polymer or copolymer thereof.

14. The organic fluorescent material of claim 11 wherein the matrix material is a solvent for the 2-benzazolyl compound.

15. The organic fluorescent material of claim 12 wherein the solid polymeric material comprises one or more aromatic polymer(s) or copolymer(s).

16. The organic fluorescent material of claim 15 wherein the aromatic polymer is polystyrene or polyvinyltoluene.

17. The organic fluorescent material of claim 15 wherein the solid polymeric material is a copolymer of styrene and/or vinyltoluene with a C$_2$ to C$_{20}$ alkylstyrene, or divinylbenzene.

18. The organic fluorescent material of claim 12 wherein the solid polymeric material comprises one or more acrylic polymer(s) or copolymer(s) having dissolved therein an aromatic compound.

19. The organic fluorescent material of claim 18 wherein the acrylic polymer is poly(methyl methacrylate) and the aromatic compound is naphthalene.

20. The organic fluorescent material of claim 12 wherein the solid polymeric material is a condensation polymer.

21. The organic fluorescent material of claim 20 wherein the condensation polymer is polycarbonate.

* * * * *